| United States Patent [19] | [11] Patent Number: 4,662,933 |
|---|---|
| Thompson | [45] Date of Patent: May 5, 1987 |

[54] HERBICIDAL SULFONAMIDES

[75] Inventor: Mark E. Thompson, Wilmington, Del.

[73] Assignee: E. I. Du Pont de Nemours and Company, Wilmington, Del.

[21] Appl. No.: 703,670

[22] Filed: Feb. 21, 1985

[51] Int. Cl.$^4$ ............... C07D 401/12; C07D 403/12; A01N 47/36
[52] U.S. Cl. .......................................... 71/92; 71/93; 544/209; 544/212; 544/253; 544/278; 544/320; 544/321; 544/323; 544/331; 544/332; 546/276; 548/265; 548/268
[58] Field of Search ............... 544/321, 322, 331, 332, 544/209, 212, 253, 278, 320, 323, 324; 71/92, 93; 546/276; 548/265, 268

[56] References Cited

U.S. PATENT DOCUMENTS

| 4,397,679 | 8/1983 | Savers | 71/92 |
|---|---|---|---|
| 4,486,589 | 12/1984 | Farnham | 544/321 |

FOREIGN PATENT DOCUMENTS

| 106512 | 4/1984 | European Pat. Off. | 71/90 |
|---|---|---|---|
| 842722 | 11/1984 | South Africa | 71/90 |

*Primary Examiner*—Robert Gerstl

[57] ABSTRACT

Benzenesulfonamide compounds such as 2-[[(4,6-dimethoxypyrimidin-2-yl)aminocarbonyl]aminosulfonyl]-N,N-dimethylbenzeneethanesulfonamide and 2-[[(4-methoxy-6-methyl-1,3,5-triazin-2-yl)aminocarbonyl]aminosulfonyl]-N,N-dimethylbenzeneethanesulfonamide, agricultural compositions containing them and their herbicidal utility are disclosed.

14 Claims, No Drawings

HERBICIDAL SULFONAMIDES

BACKGROUND OF THE INVENTION

The compounds of this invention are highly active as preemergent and/or postemergent herbicides or plant growth regulants. They are especially useful for the control of grasses, broadleaves and sedges with a high degree of rice selectivity.

U.S. Pat. No. 4,397,679 discloses herbicidal sulfonamides of formula

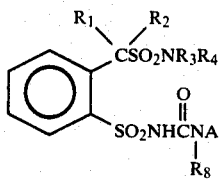

European patent application (EP-A) No. 44,209 discloses, in part, herbicidal sulfonamides of formula

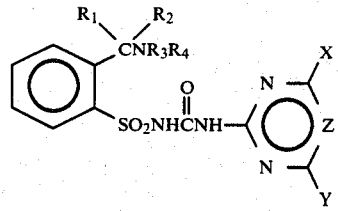

Sourth African patent application No. 83/4956 discloses, in part, herbicidal sulfonamides of formula

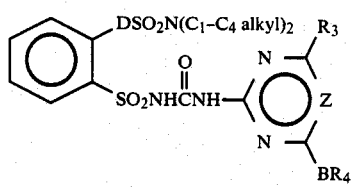

wherein
B and D are independently a single chemical bond, methylene or ethylene group, which can be substituted or unsubstituted; and
$R_4$ is $C(O)R_7$ or a functional derivative thereof.

EP-A-106,512 discloses, in part, herbicidal sulfonamides of formula

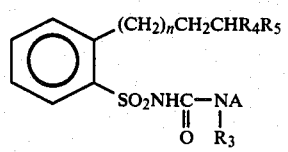

wherein
n is 0 or 1;
$R_4$ is H, F, Cl, Br or $CH_3$; and
$R_5$ is F, Cl, Br, $OC(O)R_6$, $OC(O)CF_3$, OH, $OCH_2Ph$, $OSO_2R_6$, $OSO_2CF_3$, $OSO_2C_6H_5R_7$, $S(O)_mR_6$, $OSO_2N(CH_3)_2$ or $CO_2R_8$.

South African patent application 83/6449 discloses, in part, herbicidal sulfonamides of formula

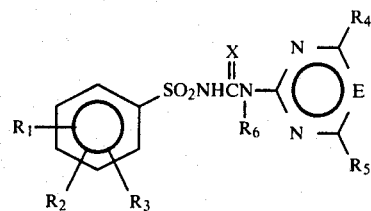

wherein
$R_3$ is a $C_2$-$C_{10}$ alkenyl group which is substituted by one or more fluorine or bromine atoms or by one or more hydroxyl, cyano, nitro, $-(Y)_mCO(Z)_nR_8$, $-SO_2NR_{11}R_{12}$, $-S(O)_pC_1-C_3$ haloalkyl or $-S(O)_nC_1-C_3$ alkyl groups and which may additionally be substituted by one or more chlorine atom.

South African patent application No. 84/2722 discloses, in part, herbicidal sulfonamides of formula

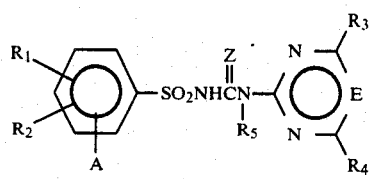

wherein
A is a radical of the formula $CR_6R_7XR_8$, $CR_9R_{10}R_{11}$ or $CHR_7SCQR_{21}$;
$R_1$ is hydrogen, halogen, nitro, cyano, $C_1-C_4$ alkyl, $C_1-C_4$ haloalkyl, $YR_{14}$, $CONR_{12}R_{13}$, $NR_{12}R_{13}$, $SONR_{15}R_{16}$, $OSO_2R_{17}$ or $COR_{18}$;
$R_2$ is hydrogen, halogen, $C_1-C_4$ alkyl, $C_1-C_4$ alkoxy, $C_1-C_4$ alkylthio, $C_1-C_4$ alkylsulfonyl or $C_1-C_4$ alkylsulfonyl;
$R_3$ and $R_4$, independently of one another, are each hydrogen, halogen, $C_1-C_4$ alkyl, $C_1-C_4$ haloalkyl, $C_1-C_4$ alkoxy, $C_1-C_4$ haloalkoxy, $C_1-C_4$ alkylthio, $C_1-C_4$ haloalkylthio, $C_2-C_5$ alkoxyalkyl or $NR_{19}R_{20}$;
$R_9$ is hydrogen, halogen, $C_1-C_4$ alkyl, $C_1-C_4$ alkoxy, $C_1-C_4$ alkylthio, $C_1-C_4$ alkylsulfinyl or $C_1-C_4$ alkylsulfonyl;
$R_{10}$ is hydrogen, halogen or methyl;
$R_{11}$ is a radical $COR_{24}$ or a $C_1-C_4$ alkyl group that is mono- or polysubstituted by substituents selected from the group: cyano, nitro, hydroxyl, $C_1-C_4$ alkoxy, $C_1-C_4$ alkylthio, etc.
$R_{18}$ is H, $C_1-C_4$ alkoxy, $NR_{12}R_{13}$, $SO_2NR_{15}R_{16}$ and various other organic radicals.

SUMMARY OF THE INVENTION

This invention pertains to novel compounds of Formula I, agriculturally suitable compositions containing them and their method-of-use as general and/or selective preemergent and/or postemergent herbicides or plant growth regulants.

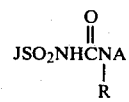

wherein
J is

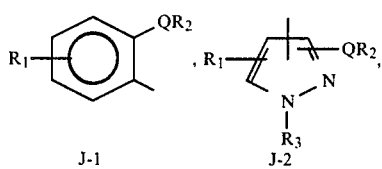

J-1, J-2

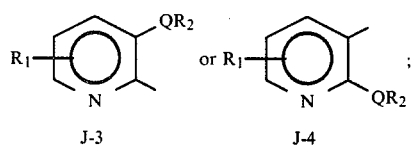

J-3, J-4

R is H or CH$_3$;

R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$-C$_3$ alkylsulfinyl, C$_1$-C$_3$ alkylsulfonyl, CN, CO$_2$R$_c$, C$_1$-C$_3$ haloalkoxy or C$_1$-C$_3$ haloalkylthio;

R$_a$ is H, C$_1$-C$_4$ alkyl, C$_2$-C$_3$ cyanoalkyl, methoxy or ethoxy;

R$_b$ is H, C$_1$-C$_4$ alkyl or C$_3$-C$_4$ alkenyl; or

R$_a$ and R$_b$ may be taken together as —(CH$_2$)$_3$—, —(CH$_2$)$_4$—, —(CH$_2$)$_5$— or —CH$_2$CH$_2$OCH$_2$CH$_2$—;

R$_c$ is C$_1$-C$_4$ alkyl, C$_3$-C$_4$ alkenyl, C$_3$-C$_4$ alkynyl, C$_2$-C$_4$ haloalkyl, C$_2$-C$_3$ cyanoalkyl, C$_5$-C$_6$ cycloalkyl, C$_4$-C$_7$ cycloalkylalkyl or C$_2$-C$_4$ alkoxyalkyl;

Q is —(CH$_2$)$_n$— which may be optionally substituted with 1-3 substituents selected from the group consisting of C$_1$-C$_3$ alkyl, C$_1$-C$_3$ alkoxy, C$_1$-C$_3$ haloalkyl, C$_1$-C$_3$ thioalkyl, halogen, cyano or NO$_2$;

n is 1, 2 or 3;

R$_2$ is SO$_2$NR$_4$R$_5$, NR$_4$R$_5$, SCN, SH or N$_3$;

R$_3$ is H, C$_1$-C$_3$ alkyl or phenyl;

R$_4$ and R$_5$ are independently H, C$_1$-C$_4$ alkyl, C$_1$-C$_4$ haloalkyl, C$_3$-C$_6$ cycloalkyl, C$_2$-C$_4$ alkoxyalkyl, C$_2$-C$_4$ alkylthioalkyl, C$_2$-C$_4$ cyanoalkyl, C$_1$-C$_3$ alkoxy, C$_3$-C$_4$ alkenyl or C$_3$-C$_4$ alkynyl; or R$_4$ and R$_5$ may be taken together to form —(CH$_2$)$_3$—, —(CH$_2$)$_4$—, —(CH$_2$)$_5$— or —CH$_2$CH$_2$OCH$_2$CH$_2$—;

A is

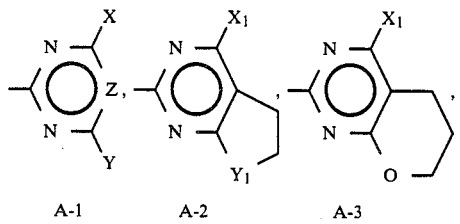

A-1, A-2, A-3

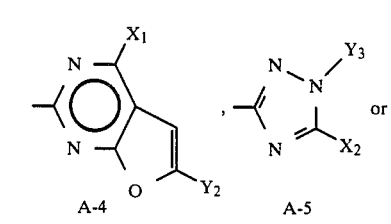

A-4, A-5

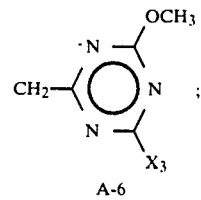

A-6

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino or di(C$_1$-C$_3$ alkyl)amino;

Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_1$-C$_4$ haloalkyl, C$_3$-C$_5$ cycloalkyl, C$_2$-C$_4$ alkynyl or N(OCH$_3$)CH$_3$;

Z is CH or N;

Y$_1$ is O or CH$_2$;

X$_1$ is CH$_3$, OCH$_3$, OC$_2$H$_5$ or OCF$_2$H;

Y$_2$ is H or CH$_3$;

X$_2$ is CH$_3$, OCH$_3$ or SCH$_3$;

Y$_3$ is CH$_3$, CH$_2$CH$_3$ or CH$_2$CF$_3$; and

X$_3$ is CH$_3$ or OCH$_3$;

and their agriculturally suitable salts; provided that (a) when X is Cl, F, Br or I, then Z is CH and Y is OCH$_3$, OC$_2$H$_6$, N(OCH$_3$)CH$_3$, NHCH$_3$, N(CH$_3$)$_2$ or OCF$_2$H;

(b) when X or Y is OCF$_2$H, then Z is CH;

(c) when R$_2$ is SO$_2$NR$_4$R$_5$, NR$_4$R$_5$ or SH, then n is 2 or 3; and (d) when J is J$_2$, then the substituent QR$_2$ and the sulfonylurea bridge are on adjacent carbon atoms.

Preferred for reasons of increased ease of synthesis and/or greater herbicidal efficacy are:

1. Compounds of Formula I where A is A-1; J is J-1; and R$_2$ is SO$_2$NR$_4$R$_5$.
2. Compounds of Preferred 1 where R$_1$ is H, C$_1$-C$_2$ alkyl, F, Cl, Br, C$_1$-C$_2$ alkoxy, C$_1$-C$_2$ alkylthio or C$_1$-C$_2$ haloalkoxy.
3. Compounds of Preferred 2 where Q is CH$_2$CH$_2$ or CH$_2$CH$_2$CH$_2$.
4. Compounds of Preferred 3 where
   X is CH$_3$, OCH$_3$, OCH$_2$CH$_3$, Cl, F, Br, I, OCF$_2$H, CH$_2$F, OCH$_2$CH$_2$F, OCH$_2$CHF$_2$, OCH$_2$CF$_3$, CF$_3$, CH$_2$Cl or CH$_2$Br; and
   Y is H, C$_1$-C$_3$ alkyl, OCH$_3$, OC$_2$H$_5$, CH$_2$OCH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, OCF$_2$H, SCF$_2$H, cyclopropyl, C≡CH or C≡CCH$_3$.
5. Compounds of Preferred 4 where Q is CH$_2$CH$_2$; and R$_4$ and R$_5$ are independently H, C$_1$-C$_3$ alkyl, C$_3$-C$_4$ alkenyl or C$_3$-C$_4$ alkynyl.
6. Compounds of Formula I where J is J-2, J-3 or J-4; and R$_2$ is SO$_2$NR$_4$R$_5$ or NR$_4$R$_5$.
7. Compounds of Preferred 6 where
   A is A-1;
   R$_1$ is H, C$_1$-C$_2$ alkyl, F, Cl, Br, C$_1$-C$_2$ alkoxy, C$_1$-C$_2$ alkylthio or C$_1$-C$_2$ haloalkoxy;
   Q is CH$_2$CH$_2$ or CH$_2$CH$_2$CH$_2$;

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$; and Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $OCF_2H$, $SCF_2H$, cyclopropyl, $C\equiv CH$ or $C\equiv CCH_3$.

8. Compounds of Preferred 7 where Q is $CH_2CH_2$; and $R_4$ and $R_5$ are independently H, $C_1$-$C_3$ alkyl, $C_3$-$C_4$ alkenyl or $C_3$-$C_4$ alkynyl.
9. Compounds of Preferred 8 where J is J-2.
10. Compounds of Preferred 8 where J is J-3 or J-4.
11. Compounds of Formula I where $R_2$ is SH, SCN or $N_3$.
12. Compounds of Preferred 12 where
   A is A-1;
   X is $CH_3$, $OCH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$;
   Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $OCF_2H$, $SCF_2H$, cyclopropyl, $C\equiv CH$ or $C\equiv CCH_3$;
   $R_1$ is H, $C_1$-$C_2$ alkyl, F, Cl, Br, $C_1$-$C_2$ alkoxy, $C_1$-$C_2$ alkylthio or $C_1$-$C_2$ haloalkoxy; and
   Q is $CH_2CH_2$ or $CH_2CH_2CH_2$.
13. Compounds of Preferred 13 where J is J-1.
14. Compounds of Preferred 13 where J is J-2.
15. Compounds of Preferred 13 where J is J-3 or J-4.

Specifically Preferred for reasons of greatest ease of synthesis and/or greatest herbicidal efficacy are:

2-[[(4,6-dimethoxypyrimidin-2-yl)aminocarbonyl]aminosulfonyl]-N,N-dimethylbenzeneethanesulfonamide, m.p. 152°-156° C.; and 2-[[(4-methoxy-6-methyl-1,3,5-triazin-2-yl)aminocarbonyl]aminosulfonyl]-N,N-dimethylbenzeneethanesulfonamide, m.p. 154°-157.5° C.

DETAILED DESCRIPTION OF THE INVENTION

Synthesis

The compounds of Formula I may be prepared as shown below in Equation 1 by the reaction of an appropriate sulfonyl isocyanate, II, with an appropriate amino heterocycle, III.

Equation 1

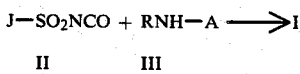

wherein
J is J-1, J-2, J-3 or J-4; and
R is H or $CH_3$.

The reaction of Equation 1 is best carried out in an inert aprotic solvent such as methylene chloride, tetrahydrofuran or acetonitrile at a temperature between 20° C. and 80° C. A catalytic amount of 1,4-diazabicyclo[2,2,2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, diethyl ether, or methanol, and filtration.

The sulfonyl isocyanates of Formula II may be prepared as shown in Equation 2, by phosgenation of the sulfonamides of Formula IV in the presence of butyl isocyanate.

Equation 2

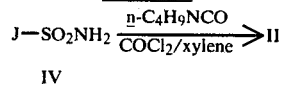

wherein
J is J-1, J-2, J-3 or J-4.

The above reaction is carried out by heating a mixture of the appropriate sulfonamide IV, an alkyl isocyanate such as butyl isocyanate and a catalytic amount of a tertiary amine such as 1,4-diazabicyclo[2,2,2]octane (DABCO) in xylene, or other inert solvent of boiling point $\geq 135°$ C., to approximately 135° C. Phosgene is then added to the mixture over a 1-6 hour period at 125°-135° C. until an excess of phosgene is present as indicated by a permanent drop in the boiling point to less than 130° C. The mixture is cooled and filtered to remove a small amount of insoluble by-products. The solvent and the alkyl isocyanate are distilled off in vacuo leaving a residue of the crude sulfonyl isocyanate, II, which can be used without further purification.

Sulfonyl isocyanates of Formula II may also be prepared as shown in Equation 3, by phosgenation of the appropriate butylureas of Formula V.

Equation 3

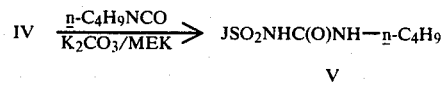

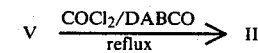

wherein
J is J-1, J-2, J-3 or J-4.

The compounds of Formula V are conveniently prepared by stirring a mixture of the sulfonamides, IV, anhydrous potassium carbonate, and n-butyl isocyanate in acetone or methyl ethyl ketone at 25°-80° C. until all of the isocyanate has reacted. The products are isolated by quenching in dilute mineral acid and recrystallizing the solid product. The compounds V are treated with phosgene and a catalytic amount of DABCO in refluxing xylene or chlorobenzene in a manner analogous to that described in Equation 2.

Sulfonyl isocyanates of Formula II may also be prepared by the two-step procedure shown below in Equation 4 starting from the appropriate sulfonamides.

Equation 4

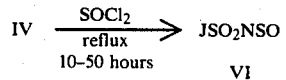

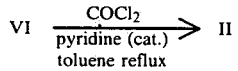

wherein

J is J-1, J-2, J-3 or J-4.

The reactions of Equation 4 (a) and (b) are best carried out according to the procedure of Ulrich et al. in *J. Org. Chem.*, 34, 3200 (1969). The sulfonamide is boiled under reflux with an excess of thionyl chloride which functions as both a reactant and solvent. When the sulfonamide protons are no longer detectable by proton NMR (15-20 hrs. on the average), the thionyl chloride is removed under reduced pressure and the residue is dissolved in an inert solvent such as toluene, benzene, xylenes, etc. A catalytic amount of pyridine is added. The mixture is treated with at least one equivalent of phosgene and heated to 60°-140° C. with 80°-100° C. preferred. Conversion to the isocyanate is substantially complete within about ¼ to 3 hours. The mixture containing the sulfonyl isocyanate can be used directly or the sulfonyl isocyanate can be isolated in pure form by filtration and evaporation of the filtrate followed by vacuum distillation if necessary.

Alternatively, compounds of Formula I may be prepared as shown in Equation 5 by the reaction of an appropriate carbamate, VII, with an appropriate amino heterocycle, III.

Equation 5

$$J-SO_2NH_2 \xrightarrow[(2) \ (PhO)_2CO]{(1) \ NaH/DMF} JSO_2NHCO_2Ph \quad (a)$$
$$IV \hspace{4cm} VII$$

$$VII + III \xrightarrow[reflux]{dioxane} I \quad (b)$$

wherein
J is J-1, J-2, J-3 or J-4; and
R is H.

The reactions of Equation 5 are best carried out according to the method described in EPO Publication 44,807.

Compounds of Formula I can be prepared by the reaction of an appropriately substituted sulfonamide, IV, with the methyl carbamate of the appropriate amino heterocycle, VIII, in the presence of an equivalent of trimethylaluminum as shown in Equation 6.

Equation 6

$$IV \xrightarrow[(2) \ RN(A)CO_2CH_3]{(1) \ Al(CH_3)_3} I$$
$$\hspace{3cm} VIII$$

wherein
J is J-1, J-2, J-3 or J-4;
R is H; and
A is as previously defined.

The reaction of Equation 6 is best carried out according to the procedure described in EPO Publication 44,210, Jan. 10, 1982.

Alternatively, as shown in Equation 7, the sulfonyl isocyanates of Formula II can be prepared by reacting the corresponding sulfonyl chloride IX with cyanic acid salts.

Equation 7

$$J-SO_2Cl \xrightarrow{M^{\oplus}OCN^{\ominus}} II$$
$$IX$$

wherein
J is J-1, J-2, J-3 or J-4.

The reaction is carried out at 25°-100° C. in an inert solvent such as acetonitrile for 0.5-24 hours in the presence of phosphorus pentoxide and an alkali metal salt such as lithium iodide according to the teachings of Japanese Pat. No. 76/26,816 (*Chem. Abst.*, 85: 77892e, (1976)).

Many of the benzene sulfonamides of Formula IV may be prepared as shown in Equation 8.

Equation 8

$$Ar-Q-OH \xrightarrow{R_6SO_2Cl} Ar-Q-OSO_2R_6 \quad (a)$$
$$X \hspace{4cm} XI$$

$$XI \longrightarrow Ar-Q-Br \quad (b)$$
$$\hspace{3cm} XII$$

$$XII \xrightarrow[reflux]{NH_2C(S)NH_2}{EtOH} Ar-Q-SCNH_2 \quad (c)$$
$$\hspace{4cm} \underset{NH_2^{\oplus}Br^{\ominus}}{\parallel}$$
$$\hspace{5cm} XIII$$

$$XIII \xrightarrow{Cl_2, H_2O} Ar-Q-SO_2Cl \quad (d)$$
$$\hspace{4cm} XIV$$

$$XIV \xrightarrow{HNR_4R_5} Ar-Q-SO_2NR_4R_5 \quad (e)$$
$$\hspace{4cm} XV$$

$$XV \xrightarrow{TFA} IV \quad (f)$$

wherein
Ar is

[structures: benzene with $SO_2NHR_7$ and $R_1$; thiophene with $R_1$ and $SO_2NHR_7$; pyrazole with $R_1$, $SO_2NHR_7$, $R_3$; pyridine with $R_1$ and $SO_2NHR_7$; or pyridine with $R_1$ and $SO_2NHR_7$]

Q is unsubstituted or substituted such that Br in Formula XII can be displaced by nucleophiles;
$R_6$ is $CH_3$ or $-C_6H_4-4-CH_3$; and
$R_7$ is H or $C(CH_3)_3$.

The conversion of alcohols such as X to the corresponding sulfonates, as shown in Equation 8a, is well known in the literature and can best be carried out according to the procedure described by A. Fürst and F. Koller, *Helv.*, 30, 1454 (1947).

The reaction of Equation 8b, displacement of sulfonates with halides is well precedented in the literature and can be effected using the methods of G. Eglinton and M. C. Whiting, *J. Chem. Soc.*, 3650, (1950); and J. Cason and J. S. Correai, *J. Org. Chem.*, 26, 3645 (1961).

The thiouronium bromide salts, XIII, can be obtained as shown in Equation 8c via the displacement of alkyl bromides with thiourea according to the methods of T. B. Johnson and J. M. Sprague, *J. Am. Chem. Soc.*, 58, 1348 (1936); 59, 1837, 2439 (1937); 61, 176 (1939).

The oxidative chlorination of thiouronium salts, Equation 8d, is most conveniently carried out by the procedure described by Johnson and Sprague, *J. Am. Chem. Soc.*, 58, 1348 (1936).

The reaction of Equation 8e is preferably carried out by treatment of a solution of the sulfonyl chloride XIV in a suitable solvent such as tetrahydrofuran or methylene chloride at $-30°$ C. to $10°$ C. with an excess of the appropriately substituted amine $HNR_4R_5$. The mixture is then stirred ambient temperature for 0.5-3 hours. The salts are washed out of the solvent with dilute hydrochloric acid and the product isolated by evaporation.

Reaction step 8f, in which the t-butyl group is cleaved, is best carried out in trifluoroacetic acid at temperatures between $25°$ C. and reflux according to the method of J. G. Lombardino [*J. Org. Chem.*, 36, 1843 (1971)].

Many of the sulfonamides of Formula IV can be prepared as shown in Equation 9.

Equation 9

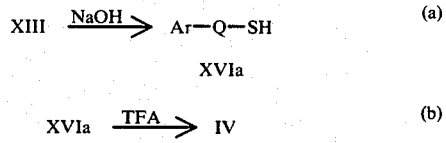

wherein

Q and Ar are as defined in Equation 8.

Mercaptans of Formula XVIa are best prepared by hydrolysis of the isothiouronium salts XIII according to the procedure described by Urquhart, Gates, and Connor, *Org. Syn., Coll. Vol.*, 3, 363 (1955).

Reaction Step 9b, in which the t-butyl group is cleaved is best carried out as described for Reaction 8f.

Certain other sulfonamides of Formula IV can be prepared as shown in Equation 10.

Equation 10

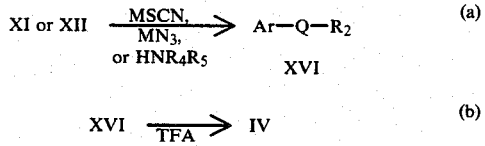

wherein

Ar and Q are as defined in Equation 8;

$R_2$ is SCN, $N_3$, or $NR_4R_5$;

$R_4$ and $R_5$ are not H; and

M is Na or K.

The conversion of sulfonates such as XI or halides such as XII to the corresponding thiocyanates ($R_2$=SCN) is well known in the literature and can be effected using the methods of Drahowzal and Klamann, *Monatsh. Chem.*, 82, 970, 973 (1951) or Saunders, Stacey, and Welding, *J. Chem. Soc.*, 775 (1949).

The displacement of sulfonates or halides with metal azide to provide sulfonamides such as XVI ($R_2=N_3$) can be carried out according to the procedures described by Boyer and Canter, *Chem. Rev.*, 54, 1-57 (1954); Bose, Kistner, and Farber *J. Org. Chem.*, 27, 2925 (1962); and Spurlock and Cox *J. Am. Chem. Soc.*, 91, 2961 (1969).

The preparation of tertiary amines such as XVI ($R_2=NR_4R_5$ where $R_4$ and $R_5$ are not H) via displacement of halides with secondary amines is widely reported in the literature for a review see: Spialter and Pappalardo, "The Acyclic Aliphatic Tertiary Amines," pp. 14-29. The Macmillan Company, New York, 1965.

Reaction step 10b, in which the t-butyl group is cleaved is best carried out as described in Reaction 8f.

Primary amines such as XVIc can be prepared as shown in Equation 11.

Equation 11

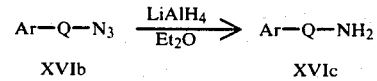

The reaction of azides to amines can be carried out by the methods of Bose, Kistner, and Farber *J. Org. Chem.*, 27, 2925 (1962) and Spurlock and Cox *J. Am. Chem. Soc.*, 91, 2961 (1969).

Many other amines such as XVI ($R_2=NR_4R_5$) can be prepared from the corresponding amides XVIII as shown in Equation 12.

Equation 12

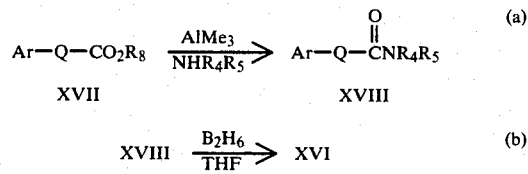

wherein

Ar is as defined in Equation 8;

Q is $-(CH_2)_n-$ which may be optionally substituted with 1-3 substituents selected from the group consisting of $C_1-C_3$ alkyl, $C_1-C_3$ alkoxy, $C_1-C_3$ haloalkoxy, $C_1-C_3$ thioalkyl, halogen, cyano or $NO_2$;

n is 1 or 2;

$R_4$ and $R_5$ are as previously defined; and $R_8$ is $CH_3$ or $CH_2CH_3$.

Amides of Formula XVIII can best be prepared via reaction of XVII with an amine in the presence of trimethylaluminum, according to the procedure described by A. Basha, M. Lipton and S. Weinreb, *Tet. Lett.*, 4171 (1977). For other pertinent synthesis of amides see "The Chemistry of Amides", J. Zabicky, Ed., Interscience, New York, 1970.

Reaction Step 12b, the reduction of amides via diborane, is best effected according to the procedure of Brown and Heim *J. Am. Chem. Soc.*, 86, 3566 (1964) and Kornet, Thio and Tan *J. Org. Chem.*, 33, 3637 (1968).

The alcohols of Formula X and the esters of Formula XVII can be prepared by one skilled in the art using the procedures taught in EP-A 106,512 and the methods described by H. W. Gschwend and H. R. Rodriguez, Organic Reactions, 26, 1 (1979).

The heterocyclic amines of Formula III in Equation 1 above can be prepared by methods known in the literature, or simple modifications thereof, by those skilled in the art. For instance, EP-A No. 84,224 (published July 27, 1983) and W. Braker et al., *J. Chem. Soc.*, 69, 3072 (1947) describes methods for preparing aminopyridines and triazines substituted by acetal groups such as dialkoxymethyl or 1,3-dioxolan-2-yl, among other groups. Also, for example, South African Patent Application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$ among other groups. South African Patent Application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuroi[2.3-d]pyrimidine-2-amines (III, A is A-2, $Y_1$ is O), the cyclopenta[d]pyrimidines-2-amines (III, A is A-2, $Y_1$ is $CH_2$) and the 6,7-dihydro-5H-pyrano[2.3-d]pyrimidin-2-amines (III, A is A-3) can be prepared as described in EP-A No. 15,683. The furo[2.3-d]pyrimidin-2-amines (III, A is A-4) are described in EP-A No. 46,677.

Compounds of Formula III, where A is A-5, are described in EP-A-73,562. Compounds of Formula III, where A is A-6, are described in EP-A-94,260.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be affected by passing an aqueous solution of a salt of a coimpound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

2-(2-Hydroxyethyl)-N-(1,1-dimethylethyl)benzenesulfonamide

A solution of N-(1,1-dimethylethyl)benzenesulfonamide (40.0 g) in 550 ml dry tetrahydrofuran was cooled to 0° and 250 ml of 1.6M n-butyllithium added dropwise at 0°. After the addition of one equivalent of base, the solution turned yellow. After stirring for 2 hours at room temperature, the resulting suspension was cooled to 0° and 13 ml of ethylene oxide added dropwise. After stirring for 3.5 hours at room temperature, the homogeneous yellow solution was poured into water. The product was extracted with ether and dried ($Na_2SO_4$). Concentration gave a yellow oil which was purified by column chromatography [400 g silica gel, ether/hexane (1:1) followed by ethyl acetate]. Pure 2-(2-hydroxyethyl)-N-(1,1-dimethylethyl)benzenesulfonamide was obtained as a colorless oil which solidified after several days; m.p. 43°–45°.

NMR ($CDCl_3$) δ: 8.09 (1H, d); 7.19–7.68 (3H, m); 5.55 (1H, s); 3.98 (2H, m); 3.31 (2H, t, J=7 Hz); 3.01 (1H, t, OH); and 1.25 (9H, s, $C(CH_3)_3$).

IR (neat) 3400, 3200, 1300, 1140 $cm^{-1}$.

EXAMPLE 2

2-[2-(Methylsulfonyloxy)ethyl]-N-)(1,1-dimethylethyl)-benzenesulfonamide

The alcohol from Example 1 (33.1 g) and 20 ml of triethylamine were dissolved in 350 ml of dichloromethane, cooled to 0° C., and treated with 11 ml methanesulfonyl chloride. After being stirred at room temperature for about 20 hours, the reaction mixture was diluted with dichloromethane (100 ml) and the organic layer was washed with three 50-ml portions of water and one of brine. Drying and concentration in vacuo gave the crude product which gradually crystallized upon standing. The solid was washed with diethyl ether, filtered, and dried to yield 12.0 g of 2-[2-(methylsulfonyloxy)ethyl]-N-(1,1-dimethylethyl)benzenesulfonamide as a white powder; m.p. 106°–108° C.

NMR ($CDCl_3$): δ 8.08–8.27 (1H, m); 7.30–7.65 (3H, m); 4.93 (1H, br s, NH); 4.59 (2H, t, J=7 Hz); 3.52 (2H, t, J=7 Hz); 2.95 (3H, s, $-OSO_2CH_3$); and 1.28 (9H, s, $C(CH_3)_3$).

EXAMPLE 3

2-(2-Bromoethyl)-N-(1,1-dimethylethyl)benzenesulfonamide

A mixture of 8.0 g of the product from Example 2, 4.9 g sodium bromide and 1.0 g potassium bromide in methyl ethyl ketone was heated at reflux temperature for approximately 24 hours. The reaction solution was allowed to cool to room temperature and was filtered to remove the insoluble salts. Evaporation of the filtrate under reduced pressure gave the crude bromide as a yellow oil. Purification by silica gel chromatography (elution with hexanes-ethyl acetate, 60:40) afforded 6.4 g of pure 2-(2-bromoethyl)-N-(1,1-dimethylethyl)benzenesulfonamide as a viscous, colorless oil.

NMR ($CDCl_3$): δ 8.0–8.2 (1H, m); 7.3–7.6 (3H, m); 5.0 (1H, br s, NH); 3.6 (4H, br t, $-CH_2CH_2-$); and 1.2 (9H, s, t-Bu).

EXAMPLE 4

[2-(2-N-(1,1-Dimethylethyl)aminosulfonyl]phenyl)ethyl]carbamimidothioic acid ester hydrobromide A solution of 2.0 g of the product from Example 3, 0.47 g of thiourea and 12 ml of absolute ethanol was heated at reflux for 3 hours then stirred at room temperature for approximately 13 hours. The solvent was removed in vacuo and the resulting white solid washed with n-butyl chloride to provide 1.8 g of [2-(2-[N-(1,1-dimethylethyl)aminosulfonyl]phenyl)ethyl]carbamimidothioic acid ester hydrobromide as a white solid; m.p. 160°-167° C.

NMR (CDCl$_3$+DMSO-d$_6$): δ 9.1 (3H, br s); 8.1 (1H, br d); 7.4–7.7 (3H, m); 3.5 (4H, br s); and 1.25 (9H, s).

EXAMPLE 5

2-[N'-(1,1-dimethylethyl)aminosulfonyl]-N,N-dimethylbenzeneethanesulfonamide

To a 0° C. solution of 8.3 g of the salt from Example 4 and 52 ml of 50% aqueous acetic acid was added dropwise 5 ml of chlorine. After the addition was complete, the cloudy orangish-yellow mixture was stirred for 2 hours at room temperature. The aqueous layer was extracted 4 times with methylene chloride. The combined organic phase was washed three times with saturated aqueous sodium bicarbonate. Drying and concentration gave 4.6 g of 2-[N-(1,1-dimethylethyl)aminosulfonyl]benzeneethanesulfonyl chloride as a green oil. The oil was dissolved in 30 ml of dry THF and the solution cooled to −10° C. Dimethylamine was added and the mixture stirred at room temperature for 3 hours. Filtration of the insoluble salts and washing with methylene chloride followed by drying afforded 3.2 g of 2-[N'-(1,1-dimethylethyl)aminosulfonyl]-N,N-dimethylbenzeneethanesulfonamide as a pale yellow oil.

NMR (CDCl$_3$): δ8.1 (1H, br d); 7.5–7.3 (3H, m); 5.2 (1H, br s, NH); 3.3–3.7 (4H, m); 2.9 (6H, s); and 1.25 (9H, s).

EXAMPLE 6

2-(Aminosulfonyl)-N,N-dimethylbenzeneethanesulfonamide

A solution of 3.2 g of the product from Example 5, and 31 mls trifluoroacetic acid was stirred at room temperature for 24 hours. The solvent was removed in vacuo and resulting semi-solid solidified after 2 days. After stirring with diethyl ether, 2.4 g of 2-(aminosulfonyl)-N,N-dimethylbenzeneethanesulfonamide was collected as a white solid; m.p. 133.5°-136° C.

IR(KBr): 3240 & 3340 (NH$_2$) cm$^{-1}$.

NMR (CDCl$_3$+DMSO-d$_6$): δ8.05 (1H, m); 7.4–7.6 (3H, m); 6.9 (2H, br s); 3.3–3.7 (4H, m); and 2.9 (6H, s).

EXAMPLE 7

N-[(4,6-Dimethoxypyrimidin-2-yl)aminocarbonyl]-2-(2-[N',N'-dimethylaminosulfonyl]ethyl)benzenesulfonamide To a suspension of 0.6 g of the product of Example 6 and 10 ml dichloroethane was added 1.2 ml of trimethylaluminum. The suspension was heated to 45°, forming a clear solution. After cooling to room temperature, 0.52 g of N-(4,6-dimethoxypyrimidin-2-yl)methyl carbamate was added and the solution heated at reflux for 24 hours. After cooling, 5% hydrochloric acid was added to obtain a pH of 3. The addition of water and methylene chloride resulted in an emulsion which was filtered through Celite. The aqueous phase was extracted an additional three times with ethyl acetate. The combined organic phases were dried, treated with charcoal, filtered and concentrated to a foam, which was triturated with n-BuCl/EtOAc to provide a white solid; m.p. 152°-156° C.

IR(KBr): 1720 (C=O) cm$^{-1}$.

NMR (CDCl$_3$): δ12.8 (1H, br s, NH); 8.2 (1H, m); 7.3–7.7 (4H, m); 5.8 (1H, s); 4.0 (6H, s); 3.3–3.7 (4H, m); and 2.9 (6H, s).

EXAMPLE 8

[2-(2-[N-(1,1-Dimethylethyl)aminosulfonyl]phenyl)ethyl]thiocyanic acid ester

A mixture of 25.0 g of the product from Example 2, 25.0 g of sodium thiocyanate and 500 ml methyl ethyl ketone was heated at reflux for 6.5 hours. The reaction solution was allowed to cool to room temperature and was filtered to remove insoluble salts. The filtrate was poured into water and extracted with methylene chloride. The organic phase was dried over Na$_2$SO$_4$ and concentrated to provide 25 g of a colorless oil.

IR(neat): 3300 (NH); 2150 (SCN) cm$^{-1}$.

NMR (CDCl$_3$): δ8.08–8.24 (1H, m); 7.33–7.73 (3H, m); 4.96 (1H, br s, NH); 3.16–3.66 (4H, m); and 1.27 (9H, s).

EXAMPLE 9

[2-(2-[Aminosulfonyl[phenyl)ethyl]thiocyanic acid ester

A solution of 24.0 g of the oil from Example 8, 2.4 g p-toluenesulfonic acid and 500 ml of toluene were heated at reflux for 3 hours. After cooling, toluene was removed in vacuo and the remaining oil triturated with n-BuCl/hexane. The resulting solid was collected by filtration to provide 5.14 g of [2-(2-[aminosulfonyl]-phenyl)ethyl]thiocyanic acid ester as an off-white solid; m.p. 87°-91° C.

IR(Nujol): 3230, 3330 (NH$_2$); 2150 (SCN) cm$^{-1}$.

NMR (CDCl$_3$): δ8.10 (1H, d); 7.40–7.70 (3H, m); 3.20–3.38 (2H, m); and 3.50–3.60 (2H, m).

EXAMPLE 10

N-[(4-Methoxy-6-methylpyrimidin-2-yl)aminocarbonyl]-2-(thiocyanatoethyl)benzenesulfonamide To a suspension of 0.5 g of the product from Example 9 and 3 ml of acetonitrile was added 0.31 ml of 1,8-diazabicyclo[5.4.0]undec-7-ene. The resulting solution was allowed to stir at room temperature for 15 minutes. To this solution 0.54 g of N-(4-methoxy-6-methylpyrimidin-2-yl)phenyl carbamate was added. After 1 hour, the solution was poured into water, acidified with 10% HCl and extracted with methylene chloride. The organic phase was washed with water then dried over Na$_2$SO$_4$. Concentration provided an oil which was triturated with n-BuCl to provide 0.33 g of N-[(4-methoxy-6-methylpyrimidin-2-yl)aminocarbonyl]-2-(thiocyanatoethyl)benzenesulfonamide as a white solid; m.p. 161°-165° C.

IR(Nujol): 2150 (SCN); 1720 (C=O) cm$^{-1}$.

NMR (DMSO): δ13.64 (1H, s, NH); 10.65 (1H, s, NH); 8.05 (1H, d); 7.60–7.75 (1H, m); 7.48–7.60 (2H, m); 6.55 (1H, s); 3.90 (3H, s); 3.40 (4H, s); and 2.38 (3H, s).

| General Structures for Tables | |
|---|---|
| General Structure 1a | 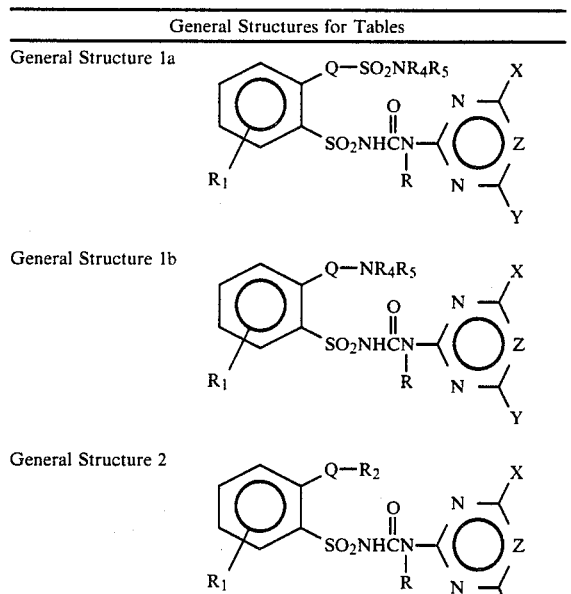 |
| General Structure 1b | |
| General Structure 2 | |

| General Structures for Tables (continued) | |
|---|---|
| General Structure 3 | 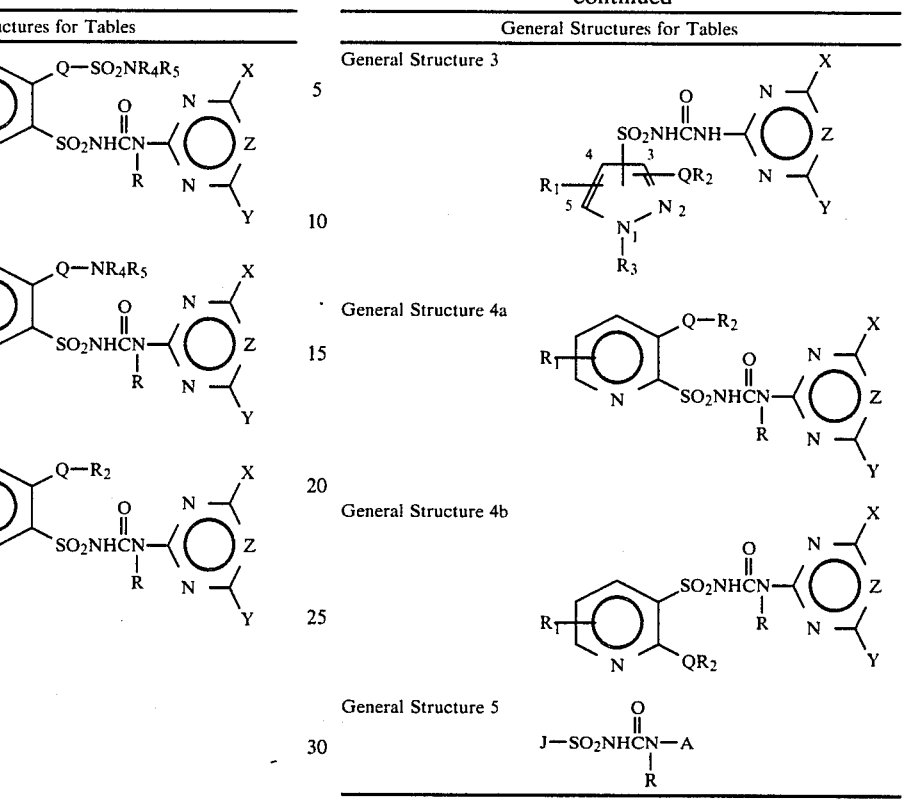 |
| General Structure 4a | |
| General Structure 4b | |
| General Structure 5 | |

TABLE 1a

General Structure 1a wherein R is H

| Q | R₁ | R₄ | R₅ | X | Y | Z | m. p. (°C.) |
|---|---|---|---|---|---|---|---|
| CH₂CH₂ | H | CH₃ | CH₃ | CH₃ | CH₃ | CH | |
| CH₂CH₂ | H | CH₃ | CH₃ | OCH₃ | CH₃ | CH | 152–155.5 |
| CH₂CH₂ | H | CH₃ | CH₃ | OCH₃ | OCH₃ | CH | 152–156 |
| CH₂CH₂ | H | CH₃ | CH₃ | Cl | OCH₃ | CH | |
| CH₂CH₂ | H | CH₃ | CH₃ | CH₃ | CH₃ | N | |
| CH₂CH₂ | H | CH₃ | CH₃ | CH₃ | OCH₃ | N | 154–157.5 |
| CH₂CH₂ | H | CH₃ | CH₃ | OCH₃ | OCH₃ | N | |
| CH₂CH₂ | H | H | CH₃ | CH₃ | OCH₃ | CH | |
| CH₂CH₂ | H | H | CH₃ | OCH₃ | OCH₃ | CH | |
| CH₂CH₂ | H | H | CH₃ | Cl | OCH₃ | CH | |
| CH₂CH₂ | H | H | CH₃ | CH₃ | OCH₃ | N | |
| CH₂CH₂ | H | H | CH₃ | OCH₃ | OCH₃ | N | |
| CH₂CH₂ | H | H | CH₂CH₃ | CH₃ | OCH₃ | CH | |
| CH₂CH₂ | H | H | n-C₃H₇ | OCH₃ | OCH₃ | CH | |
| CH₂CH₂ | H | H | i-C₃H₇ | CH₃ | OCH₃ | N | |
| CH₂CH₂ | H | H | CH₂Cl | OCH₃ | OCH₃ | N | |
| CH₂CH₂ | H | H | CH₂CH₂Cl | OCH₃ | OCH₃ | N | |
| CH₂CH₂ | H | H | CH₂CH₂Br | CH₃ | OCH₃ | CH | |
| CH₂CH₂ | H | H | CH₂CH₂F | OCH₃ | OCH₃ | CH | |
| CH₂CH₂ | H | H | cyclopropyl | CH₃ | OCH₃ | N | |
| CH₂CH₂ | H | H | CH₂-cyclopropyl | OCH₃ | OCH₃ | N | |
| CH₂CH₂ | H | H | cyclobutyl | CH₃ | OCH₃ | CH | |
| CH₂CH₂ | H | H | cyclopentyl | OCH₃ | OCH₃ | CH | |
| CH₂CH₂ | H | H | cyclohexyl | Cl | OCH₃ | CH | |
| CH₂CH₂ | H | H | CH₂OCH₃ | CH₃ | OCH₃ | CH | |
| CH₂CH₂ | H | H | CH₂OCH₂CH₃ | Cl | OCH₃ | CH | |
| CH₂CH₂ | H | H | CH₂CH₂OCH₃ | CH₃ | OCH₃ | N | |
| CH₂CH₂ | H | H | CH₂CH₂OC₂H₅ | OCH₃ | OCH₃ | N | |
| CH₂CH₂ | H | H | CH₂SCH₃ | CH₃ | OCH₃ | CH | |
| CH₂CH₂ | H | H | CH₂CH₂SCH₃ | OCH₃ | OCH₃ | CH | |
| CH₂CH₂ | H | H | OCH₃ | CH₃ | OCH₃ | N | |
| CH₂CH₂ | H | H | OC₂H₅ | OCH₃ | OCH₃ | N | |
| CH₂CH₂ | H | H | O-n-C₃H₇ | CH₃ | OCH₃ | CH | |
| CH₂CH₂ | H | H | CH₂CH=CH₂ | OCH₃ | OCH₃ | CH | |
| CH₂CH₂ | H | H | CH₂CH₂CH=CH₂ | Cl | OCH₃ | CH | |
| CH₂CH₂ | H | H | Prop-1-yne | CH₃ | OCH₃ | N | |
| CH₂CH₂ | H | H | but-1-yne | OCH₃ | OCH₃ | N | |
| CH₂CH₂ | H | CH₃ | C₂H₅ | CH₃ | OCH₃ | CH | |

TABLE 1a-continued

General Structure 1a wherein R is H

| Q | $R_1$ | $R_4$ | $R_5$ | X | Y | Z | m. p. (°C.) |
|---|---|---|---|---|---|---|---|
| $CH_2CH_2$ | H | $CH_3$ | $\underline{n}$-$C_3H_7$ | $OCH_3$ | $OCH_3$ | CH | |
| $CH_2CH_2$ | H | $CH_3$ | $OCH_3$ | Cl | $OCH_3$ | CH | |
| $CH_2CH_2$ | H | $C_2H_5$ | $C_2H_5$ | $OCH_3$ | $OCH_3$ | N | |
| $CH_2CH_2$ | H | \-$CH_2CH_2CH_2CH_2$\- | | $CH_3$ | $OCH_3$ | CH | |
| $CH_2CH_2$ | H | \-$CH_2CH_2OCH_2CH_2$\- | | $OCH_3$ | $OCH_3$ | CH | |
| $CH_2CH_2$ | H | \-$(CH_2)_5$\- | | Cl | $OCH_3$ | CH | |
| $CH_2CH_2$ | 3-$CH_3$ | $CH_3$ | $CH_3$ | $CH_3$ | $OCH_3$ | N | |
| $CH_2CH_2$ | 5-$CH_2Cl$ | $CH_3$ | $CH_3$ | $OCH_3$ | $OCH_3$ | N | |
| $CH_2CH_2$ | 5-Cl | $CH_3$ | $CH_3$ | $CH_3$ | $OCH_3$ | CH | |
| $CH_2CH_2$ | 4-$NO_2$ | $CH_3$ | $CH_3$ | $OCH_3$ | $OCH_3$ | CH | |
| $CH_2CH_2$ | 5-$OCH_3$ | $CH_3$ | $CH_3$ | Cl | $OCH_3$ | CH | |
| $CH_2CH_2$ | 3-$SO_2N(CH_3)_2$ | $CH_3$ | $CH_3$ | $CH_3$ | $OCH_3$ | N | |
| $CH_2CH_2$ | 3-$SCH_3$ | $CH_3$ | $CH_3$ | $OCH_3$ | $OCH_3$ | CH | |
| $CH_2CH_2$ | 5-$SCH_3$ | $CH_3$ | $CH_3$ | $CH_3$ | $OCH_3$ | CH | |
| $CH_2CH_2$ | 4-$SOCH_3$ | $CH_3$ | $CH_3$ | $CH_3$ | $OCH_3$ | N | |
| $CH_2CH_2$ | 5-$SO_2CH_3$ | $CH_3$ | $CH_3$ | $OCH_3$ | $OCH_3$ | CH | |
| $CH_2CH_2$ | 3-$CO_2CH_3$ | $CH_3$ | $CH_3$ | $OCH_3$ | $OCH_3$ | N | |
| $CH_2CH_2$ | 4-$OCH_2CH_2Cl$ | $CH_3$ | $CH_3$ | $CH_3$ | $OCH_3$ | CH | |
| $CH_2CH_2$ | 3-$SCH_2CH_2Cl$ | $CH_3$ | $CH_3$ | $OCH_3$ | $OCH_3$ | CH | |
| $CH_2CH_2$ | 6-CN | $CH_3$ | $CH_3$ | Cl | $OCH_3$ | CH | |
| $CH_2CH(CH_3)$ | H | $CH_3$ | $CH_3$ | $CH_3$ | $OCH_3$ | N | |
| $CH(CH_3)CH_2$ | H | $CH_3$ | $CH_3$ | $CH_3$ | $OCH_3$ | CH | |
| $CH(CH_3)CH(CH_3)$ | H | $CH_3$ | $CH_3$ | $OCH_3$ | $OCH_3$ | CH | |
| $CH(C_2H_5)CH_2$ | H | $CH_3$ | $CH_3$ | $OCH_3$ | $OCH_3$ | CH | |
| $CH(OCH_3)CH_2$ | H | $CH_3$ | $CH_3$ | $OCH_3$ | $OCH_3$ | CH | |
| $CH(OCH_3)CH(CH_3)$ | H | $CH_3$ | $CH_3$ | $OCH_3$ | $OCH_3$ | CH | |
| $CH(SCH_3)CH_2$ | H | $CH_3$ | $CH_3$ | $OCH_3$ | $OCH_3$ | CH | |
| $CH(SCH_3)CH(CH_3)$ | H | $CH_3$ | $CH_3$ | $OCH_3$ | $OCH_3$ | CH | |
| $CH(Cl)CH_2$ | H | $CH_3$ | $CH_3$ | $OCH_3$ | $OCH_3$ | CH | |
| $CH_2CH_2CH_2$ | H | $CH_3$ | $CH_3$ | $OCH_3$ | $OCH_3$ | CH | |
| $CH_2CH_2CH(CH_3)$ | H | $CH_3$ | $CH_3$ | $OCH_3$ | $OCH_3$ | CH | |
| $CH(CH_3)CH_2CH_2$ | H | $CH_3$ | $CH_3$ | $OCH_3$ | $OCH_3$ | CH | |
| $CH(OCH_3)CH_2CH_2$ | H | $CH_3$ | $CH_3$ | $OCH_3$ | $OCH_3$ | CH | |
| $CH(SCH_3)CH_2CH_2$ | H | $CH_3$ | $CH_3$ | $OCH_3$ | $OCH_3$ | CH | |
| $CH(Cl)CH_2CH_2$ | H | $CH_3$ | $CH_3$ | $OCH_3$ | $OCH_3$ | CH | |
| $CH(CN)CH_2$ | H | $CH_3$ | $CH_3$ | $OCH_3$ | $OCH_3$ | CH | |
| $CH(CN)CH_2CH_2$ | H | $CH_3$ | $CH_3$ | $OCH_3$ | $OCH_3$ | CH | |
| $CH(NO_2)CH_2$ | H | $CH_3$ | $CH_3$ | $OCH_3$ | $OCH_3$ | CH | |
| $CH_2CH_2$ | H | $CH_3$ | $CH_3$ | $OCH_3$ | $OC_2H_5$ | CH | |
| $CH_2CH_2$ | H | $CH_3$ | $CH_3$ | $CH_3$ | $OC_2H_5$ | CH | |
| $CH_2CH_2$ | H | $CH_3$ | $CH_3$ | $CH_3$ | $OCH_2Cl$ | CH | |
| $CH_2CH_2$ | H | $CH_3$ | $CH_3$ | $CH_3$ | $OCH_2CH_2Cl$ | CH | |
| $CH_2CH_2$ | H | $CH_3$ | $CH_3$ | $OCH_3$ | $CH_2Cl$ | CH | |
| $CH_2CH_2$ | H | $CH_3$ | $CH_3$ | $OCH_3$ | $CH_2CH_2Cl$ | CH | |
| $CH_2CH_2$ | H | $CH_3$ | $CH_3$ | $CH_3$ | $SCH_2Cl$ | CH | |
| $CH_2CH_2$ | H | $CH_3$ | $CH_3$ | $OCH_3$ | Br | CH | |
| $CH_2CH_2$ | H | $CH_3$ | $CH_3$ | $OCH_3$ | F | CH | |
| $CH_2CH_2$ | H | $CH_3$ | $CH_3$ | $OCH_3$ | I | CH | |
| $CH_2CH_2$ | H | $CH_3$ | $CH_3$ | $CH_3$ | $CH_2OCH_3$ | CH | |
| $CH_2CH_2$ | H | $CH_3$ | $CH_3$ | $CH_3$ | $CH(OCH_3)_2$ | CH | |
| $CH_2CH_2$ | H | $CH_3$ | $CH_3$ | $CH_3$ | 1,3-dioxolan-2-yl | CH | |
| $CH_2CH_2$ | H | $CH_3$ | $CH_3$ | $CH_3$ | 1,3-dioxan-2-yl | CH | |
| $CH_2CH_2$ | H | $CH_3$ | $CH_3$ | $CH_3$ | $OCH_2OCH_3$ | CH | |
| $CH_2CH_2$ | H | $CH_3$ | $CH_3$ | Cl | $NH_2$ | N | |
| $CH_2CH_2$ | H | $CH_3$ | $CH_3$ | $OC_2H_5$ | $NHCH_3$ | N | |
| $CH_2CH_2$ | H | $CH_3$ | $CH_3$ | Cl | $N(CH_3)_2$ | N | |
| $CH_2CH_2$ | H | $CH_3$ | $CH_3$ | $CH_3$ | $OCH=CH_2$ | CH | |
| $CH_2CH_2$ | H | $CH_3$ | $CH_3$ | $CH_3$ | $OCH_2C\equiv CH$ | CH | |
| $CH_2CH_2$ | H | $CH_3$ | $CH_3$ | $CH_3$ | $OCH_2CF_3$ | CH | |
| $CH_2CH_2$ | H | $CH_3$ | $CH_3$ | $OCH_3$ | $CH_2F$ | CH | |
| $CH_2CH_2$ | H | $CH_3$ | $CH_3$ | $CH_3$ | $OCF_2H$ | CH | |
| $CH_2CH_2$ | H | $CH_3$ | $CH_3$ | $OCH_3$ | $N(OCH_3)CH_3$ | N | |
| $CH_2CH_2$ | H | $CH_3$ | $CH_3$ | $OCH_2CH_3$ | $NHCH_3$ | N | |

TABLE 1b

General Structure 1b wherein R is H

| Q | $R_1$ | $R_4$ | $R_5$ | X | Y | Z | m. p. (°C.) |
|---|---|---|---|---|---|---|---|
| $CH_2CH_2$ | H | $CH_3$ | $CH_3$ | $CH_3$ | $CH_3$ | CH | |
| $CH_2CH_2$ | H | $CH_3$ | $CH_3$ | $OCH_3$ | $CH_3$ | CH | |
| $CH_2CH_2$ | H | $CH_3$ | $CH_3$ | $OCH_3$ | $OCH_3$ | CH | |
| $CH_2CH_2$ | H | $CH_3$ | $CH_3$ | Cl | $OCH_3$ | CH | |
| $CH_2CH_2$ | H | $CH_3$ | $CH_3$ | $CH_3$ | $CH_3$ | N | |
| $CH_2CH_2$ | H | $CH_3$ | $CH_3$ | $CH_3$ | $OCH_3$ | N | |
| $CH_2CH_2$ | H | $CH_3$ | $CH_3$ | $OCH_3$ | $OCH_3$ | N | |

TABLE 1b-continued

General Structure 1b
wherein R is H

| Q | R₁ | R₄ | R₅ | X | Y | Z | m. p. (°C.) |
|---|---|---|---|---|---|---|---|
| CH₂CH₂ | H | H | CH₃ | CH₃ | OCH₃ | CH | |
| CH₂CH₂ | H | H | CH₃ | OCH₃ | OCH₃ | CH | |
| CH₂CH₂ | H | H | CH₃ | Cl | OCH₃ | CH | |
| CH₂CH₂ | H | H | CH₃ | CH₃ | OCH₃ | N | |
| CH₂CH₂ | H | H | CH₃ | OCH₃ | OCH₃ | N | |
| CH₂CH₂ | H | H | CH₂CH₃ | CH₃ | OCH₃ | CH | |
| CH₂CH₂ | H | H | n-C₃H₇ | OCH₃ | OCH₃ | CH | |
| CH₂CH₂ | H | H | i-C₃H₇ | CH₃ | OCH₃ | N | |
| CH₂CH₂ | H | H | CH₂Cl | OCH₃ | OCH₃ | N | |
| CH₂CH₂ | H | H | CH₂CH₂Cl | OCH₃ | OCH₃ | N | |
| CH₂CH₂ | H | H | CH₂CH₂Br | CH₃ | OCH₃ | CH | |
| CH₂CH₂ | H | H | CH₂CH₂F | OCH₃ | OCH₃ | CH | |
| CH₂CH₂ | H | H | cyclopropyl | CH₃ | OCH₃ | N | |
| CH₂CH₂ | H | H | CH₂—cyclopropyl | OCH₃ | OCH₃ | N | |
| CH₂CH₂ | H | H | cyclobutyl | CH₃ | OCH₃ | CH | |
| CH₂CH₂ | H | H | cyclopentyl | OCH₃ | OCH₃ | CH | |
| CH₂CH₂ | H | H | cyclohexyl | Cl | OCH₃ | CH | |
| CH₂CH₂ | H | H | CH₂OCH₃ | CH₃ | OCH₃ | CH | |
| CH₂CH₂ | H | H | CH₂OCH₂CH₃ | Cl | OCH₃ | CH | |
| CH₂CH₂ | H | H | CH₂CH₂OCH₃ | CH₃ | OCH₃ | N | |
| CH₂CH₂ | H | H | CH₂CH₂OC₂H₅ | OCH₃ | OCH₃ | N | |
| CH₂CH₂ | H | H | CH₂SCH₃ | CH₃ | OCH₃ | CH | |
| CH₂CH₂ | H | H | CH₂CH₂SCH₃ | OCH₃ | OCH₃ | CH | |
| CH₂CH₂ | H | H | OCH₃ | CH₃ | OCH₃ | N | |
| CH₂CH₂ | H | H | OC₂H₅ | OCH₃ | OCH₃ | N | |
| CH₂CH₂ | H | H | O—n-C₃H₇ | CH₃ | OCH₃ | CH | |
| CH₂CH₂ | H | H | CH₂CH=CH₂ | OCH₃ | OCH₃ | CH | |
| CH₂CH₂ | H | H | CH₂CH₂CH=CH₂ | Cl | OCH₃ | CH | |
| CH₂CH₂ | H | H | Prop-1-yne | CH₃ | OCH₃ | N | |
| CH₂CH₂ | H | H | but-1-yne | OCH₃ | OCH₃ | N | |
| CH₂CH₂ | H | CH₃ | C₂H₅ | CH₃ | OCH₃ | CH | |
| CH₂CH₂ | H | CH₃ | n-C₃H₇ | OCH₃ | OCH₃ | CH | |
| CH₂CH₂ | H | CH₃ | OCH₃ | Cl | OCH₃ | CH | |
| CH₂CH₂ | H | C₂H₅ | C₂H₅ | OCH₃ | OCH₃ | N | |
| CH₂CH₂ | H | —CH₂CH₂CH₂CH₂— | | CH₃ | OCH₃ | CH | |
| CH₂CH₂ | H | —CH₂CH₂OCH₂CH₂— | | OCH₃ | OCH₃ | CH | |
| CH₂CH₂ | H | —(CH₂)₅— | | Cl | OCH₃ | CH | |
| CH₂CH₂ | 3-CH₃ | CH₃ | CH₃ | CH₃ | OCH₃ | N | |
| CH₂CH₂ | 5-CH₂Cl | CH₃ | CH₃ | OCH₃ | OCH₃ | N | |
| CH₂CH₂ | 5-Cl | CH₃ | CH₃ | CH₃ | OCH₃ | CH | |
| CH₂CH₂ | 4-NO₂ | CH₃ | CH₃ | OCH₃ | OCH₃ | CH | |
| CH₂CH₂ | 5-OCH₃ | CH₃ | CH₃ | Cl | OCH₃ | CH | |
| CH₂CH₂ | 3-SO₂N(CH₃)₂ | CH₃ | CH₃ | CH₃ | OCH₃ | N | |
| CH₂CH₂ | 3-SCH₃ | CH₃ | CH₃ | OCH₃ | OCH₃ | CH | |
| CH₂CH₂ | 5-SCH₃ | CH₃ | CH₃ | CH₃ | OCH₃ | CH | |
| CH₂CH₂ | 4-SOCH₃ | CH₃ | CH₃ | CH₃ | OCH₃ | N | |
| CH₂CH₂ | 5-SO₂CH₃ | CH₃ | CH₃ | OCH₃ | OCH₃ | CH | |
| CH₂CH₂ | 3-CO₂CH₃ | CH₃ | CH₃ | OCH₃ | OCH₃ | N | |
| CH₂CH₂ | 4-OCH₂CH₂Cl | CH₃ | CH₃ | CH₃ | OCH₃ | CH | |
| CH₂CH₂ | 3-SCH₂CH₂Cl | CH₃ | CH₃ | OCH₃ | OCH₃ | CH | |
| CH₂CH₂ | 6-CN | CH₃ | CH₃ | Cl | OCH₃ | CH | |
| CH₂CH(CH₃) | H | CH₃ | CH₃ | CH₃ | OCH₃ | N | |
| CH(CH₃)CH₂ | H | CH₃ | CH₃ | CH₃ | OCH₃ | CH | |
| CH(CH₃)CH(CH₃) | H | CH₃ | CH₃ | OCH₃ | OCH₃ | CH | |
| CH(C₂H₅)CH₂ | H | CH₃ | CH₃ | OCH₃ | OCH₃ | CH | |
| CH(OCH₃)CH₂ | H | CH₃ | CH₃ | OCH₃ | OCH₃ | CH | |
| CH(OCH₃)CH(CH₃) | H | CH₃ | CH₃ | OCH₃ | OCH₃ | CH | |
| CH(SCH₃)CH₂ | H | CH₃ | CH₃ | OCH₃ | OCH₃ | CH | |
| CH(SCH₃)CH(CH₃) | H | CH₃ | CH₃ | OCH₃ | OCH₃ | CH | |
| CH(Cl)CH₂ | H | CH₃ | CH₃ | OCH₃ | OCH₃ | CH | |
| CH₂CH₂CH₂ | H | CH₃ | CH₃ | OCH₃ | OCH₃ | CH | |
| CH₂CH₂CH(CH₃) | H | CH₃ | CH₃ | OCH₃ | OCH₃ | CH | |
| CH(CH₃)CH₂CH₂ | H | CH₃ | CH₃ | OCH₃ | OCH₃ | CH | |
| CH(OCH₃)CH₂CH₂ | H | CH₃ | CH₃ | OCH₃ | OCH₃ | CH | |
| CH(SCH₃)CH₂CH₂ | H | CH₃ | CH₃ | OCH₃ | OCH₃ | CH | |
| CH(Cl)CH₂CH₂ | H | CH₃ | CH₃ | OCH₃ | OCH₃ | CH | |
| CH(CN)CH₂ | H | CH₃ | CH₃ | OCH₃ | OCH₃ | CH | |
| CH(CH)CH₂CH₂ | H | CH₃ | CH₃ | OCH₃ | OCH₃ | CH | |
| CH(NO₂)CH₂ | H | CH₃ | CH₃ | OCH₃ | OCH₃ | CH | |
| CH₂CH₂ | H | CH₃ | CH₃ | OCH₃ | OC₂H₅ | CH | |
| CH₂CH₂ | H | CH₃ | CH₃ | CH₃ | OC₂H₅ | CH | |
| CH₂CH₂ | H | CH₃ | CH₃ | CH₃ | OCH₂Cl | CH | |
| CH₂CH₂ | H | CH₃ | CH₃ | CH₃ | OCH₂CH₂Cl | CH | |
| CH₂CH₂ | H | CH₃ | CH₃ | OCH₃ | CH₂Cl | CH | |
| CH₂CH₂ | H | CH₃ | CH₃ | OCH₃ | CH₂CH₂Cl | CH | |
| CH₂CH₂ | H | CH₃ | CH₃ | CH₃ | SCH₂Cl | CH | |
| CH₂CH₂ | H | CH₃ | CH₃ | OCH₃ | Br | CH | |
| CH₂CH₂ | H | CH₃ | CH₃ | OCH₃ | F | CH | |
| CH₂CH₂ | H | CH₃ | CH₃ | OCH₃ | I | CH | |

TABLE 1b-continued

General Structure 1b wherein R is H

| Q | R₁ | R₄ | R₅ | X | Y | Z | m. p. (°C.) |
|---|---|---|---|---|---|---|---|
| CH₂CH₂ | H | CH₃ | CH₃ | CH₃ | CH₂OCH₃ | CH | |
| CH₂CH₂ | H | CH₃ | CH₃ | CH₃ | CH(OCH₃)₂ | CH | |
| CH₂CH₂ | H | CH₃ | CH₃ | CH₃ | 1,3-dioxolan-2-yl | CH | |
| CH₂CH₂ | H | CH₃ | CH₃ | CH₃ | 1,3-dioxan-2-yl | CH | |
| CH₂CH₂ | H | CH₃ | CH₃ | CH₃ | OCH₂OCH₃ | CH | |
| CH₂CH₂ | H | CH₃ | CH₃ | Cl | NH₂ | N | |
| CH₂CH₂ | H | CH₃ | CH₃ | OC₂H₅ | NHCH₃ | N | |
| CH₂CH₂ | H | CH₃ | CH₃ | Cl | N(CH₃)₂ | N | |
| CH₂CH₂ | H | CH₃ | CH₃ | CH₃ | OCH=CH₂ | CH | |
| CH₂CH₂ | H | CH₃ | CH₃ | CH₃ | OCH₂C≡CH | CH | |
| CH₂CH₂ | H | CH₃ | CH₃ | CH₃ | OCH₂CF₃ | CH | |
| CH₂CH₂ | H | CH₃ | CH₃ | OCH₃ | CH₂F | CH | |
| CH₂CH₂ | H | CH₃ | CH₃ | CH₃ | OCF₂H | CH | |
| CH₂CH₂ | H | CH₃ | CH₃ | OCH₃ | N(OCH₃)CH₃ | N | |
| CH₂CH₂ | H | CH₃ | CH₃ | OCH₂CH₃ | NHCH₃ | N | |

TABLE 1c

General Structure 1a wherein R is CH₃

| R₁ | R₄ | R₅ | X | Y | Z | m. p. (°C.) |
|---|---|---|---|---|---|---|
| H | CH₃ | CH₃ | OCH₃ | OCH₃ | N | |
| H | CH₃ | CH₃ | OCH₃ | OCH₃ | CH | |
| H | CH₃ | CH₃ | CH₃ | OCH₃ | N | |
| H | CH₃ | CH₃ | CH₃ | OCH₃ | CH | |

TABLE 1d

General Structure 1b wherein R is CH₃

| R₁ | R₄ | R₅ | X | Y | Z | m. p. (°C.) |
|---|---|---|---|---|---|---|
| H | CH₃ | CH₃ | OCH₃ | OCH₃ | N | |
| H | CH₃ | CH₃ | OCH₃ | OCH₃ | CH | |
| H | CH₃ | CH₃ | CH₃ | OCH₃ | N | |
| H | CH₃ | CH₃ | CH₃ | OCH₃ | CH | |

TABLE 2a

General Structure 2 wherein R is H

| R₁ | Q | R₂ | X | Y | Z | m.p. (°C.) |
|---|---|---|---|---|---|---|
| H | CH₂CH₂ | SCN | CH₃ | CH₃ | CH | 161-165 |
| H | CH₂CH₂ | SCN | CH₃ | OCH₃ | CH | 140-147 |
| H | CH₂CH₂ | SCN | OCH₃ | OCH₃ | CH | 167-174 |
| H | CH₂CH₂ | SCN | Cl | OCH₃ | CH | 124-141 |
| H | CH₂CH₂ | SCN | CH₃ | CH₃ | N | 113-128 |
| H | CH₂CH₂ | SCN | CH₃ | OCH₃ | N | 160-163 |
| H | CH₂CH₂ | SCN | OCH₃ | OCH₃ | N | 172-176 |
| H | CH₂CH₂ | SCN | Br | OCH₃ | CH | |
| H | CH₂CH₂ | SCN | OCH₂CH₃ | NHCH₃ | N | |
| H | CH₂CH₂ | SH | CH₃ | OCH₃ | CH | |
| H | CH₂CH₂ | SH | OCH₃ | OCH₃ | CH | |
| H | CH₂CH₂ | SH | CH₃ | OCH₃ | N | |
| H | CH₂CH₂ | SH | OCH₃ | OCH₃ | N | |
| H | CH₂CH₂ | N₃ | CH₃ | OCH₃ | N | |
| H | CH₂CH₂ | N₃ | OCH₃ | OCH₃ | N | |
| H | CH₂CH₂ | N₃ | CH₃ | OCH₃ | CH | |
| H | CH₂CH₂ | N₃ | OCH₃ | OCH₃ | CH | |
| H | CH(CH₃)CH₂ | N₃ | OCH₃ | OCH₃ | CH | |
| H | CH(OCH₃)CH₂ | N₃ | CH₃ | OCH₃ | CH | |
| H | CH₂CH(CH₃) | N₃ | CH₃ | OCH₃ | CH | |
| H | CH₂CH₂CH₂ | SCN | CH₃ | OCH₃ | CH | |
| H | CH₂CH₂CH(CH₃) | SCN | OCH₃ | OCH₃ | N | |
| H | CH(CH₃)CH₂CH₂ | SCN | CH₃ | OCH₃ | N | |
| H | CH(SCH₃)CH₂CH₂ | SCN | CH₃ | OCH₃ | N | |
| 3-CH₃ | CH₂CH₂ | SH | OCH₃ | OCH₃ | CH | |
| 5-OCH₃ | CH₂CH₂ | SH | Cl | OCH₃ | CH | |
| H | CH₂ | SCN | CH₃ | OCH₃ | CH | |
| H | CH₂ | N₃ | OCH₃ | OCH₃ | N | |
| H | CH₂ | N₃ | CH₃ | OCH₃ | CH | |

TABLE 2b

General Structure 2 wherein R is CH₃

| R₁ | Q | R₂ | X | Y | Z | m.p. (°C.) |
|---|---|---|---|---|---|---|
| H | CH₂CH₂ | SCN | OCH₃ | OCH₃ | CH | |
| H | CH₂CH₂ | SH | CH₃ | OCH₃ | CH | |
| H | CH₂CH₂ | N₃ | OCH₃ | OCH₃ | N | |

TABLE 3

General Structure 3

| $R_2$ | $R_3$ | $R_1$ | Q | a* | X | Y | Z | m.p. (°C.) |
|---|---|---|---|---|---|---|---|---|
| $SO_2N(CH_3)_2$ | $CH_3$ | H | 4-$CH_2CH_2$ | 3 | $CH_3$ | $OCH_3$ | CH | |
| SCN | $CH_3$ | H | 4-$CH_2CH_2$ | 3 | $OCH_3$ | $OCH_3$ | CH | |
| $N_3$ | $CH_3$ | H | 4-$CH_2CH_2$ | 3 | $CH_3$ | $OCH_3$ | N | |
| $N(CH_3)_2$ | $CH_3$ | 5-Cl | 4-$CH_2CH_2$ | 3 | $OCH_3$ | $OCH_3$ | N | |
| $SO_2N(CH_3)_2$ | $CH_3$ | H | 4-$CH_2CH_2$ | 3 | Cl | $OCH_3$ | CH | |
| $N(CH_3)_2$ | $CH_3$ | H | 3-$CH_2CH_2$ | 4 | $OCH_3$ | $OCH_3$ | N | |
| $SO_2N(CH_3)_2$ | $CH_3$ | 5-Cl | 3-$CH_2CH_2$ | 4 | $OCH_3$ | $OCH_3$ | CH | |
| SCN | $CH_3$ | 3-$CH_3$ | 5-$CH_2CH_2$ | 4 | $CH_3$ | $OCH_3$ | CH | |
| $N_3$ | $CH_3$ | 3-Cl | 5-$CH_2CH_2$ | 4 | Cl | $OCH_3$ | CH | |
| $SO_2N(CH_3)_2$ | $CH_3$ | 3-$CH_3$ | 4-$CH_2CH_2$ | 5 | $CH_3$ | $OCH_3$ | N | |
| SCN | $CH_3$ | 3-Cl | 4-$CH_2CH_2$ | 5 | $OCH_3$ | $OCH_3$ | N | |
| $N_3$ | H | 3-$CH_3$ | 4-$CH_2CH_2$ | 5 | $CH_3$ | $OCH_3$ | CH | |
| $N(CH_3)_2$ | $CH_3$ | H | 4-$CH_2CH_2$ | 5 | $OCH_3$ | $OCH_3$ | CH | |
| SCN | H | 3-Cl | 4-$CH_2CH_2$ | 5 | $CH_3$ | $OCH_3$ | N | |
| $N(CH_3)_2$ | $CH_3$ | H | 4-$CH(CH_3)CH_2$ | 5 | $OCH_3$ | $OCH_3$ | N | |
| SH | $CH_3$ | H | 4-$CH(SCH_3)CH_2$ | 5 | Cl | $OCH_3$ | CH | | a* = Ring Position of Bridge

TABLE 4a

General Structure 4a

| Q | R | $R_1$ | $R_2$ | X | Y | Z | m.p. (°C.) |
|---|---|---|---|---|---|---|---|
| $CH_2CH_2$ | H | H | $SO_2N(CH_3)_2$ | $CH_3$ | $CH_3$ | CH | |
| $CH_2CH_2$ | H | H | SCN | $OCH_3$ | $CH_3$ | CH | |
| $CH_2CH_2$ | H | H | $N(CH_3)_2$ | $OCH_3$ | $OCH_3$ | CH | |
| $CH_2CH_2$ | H | H | $N_3$ | Cl | $OCH_3$ | CH | |
| $CH_2CH_2$ | H | H | SH | $CH_3$ | $CH_3$ | N | |
| $CH(CH_3)CH_2$ | H | H | $SO_2NHCH_3$ | $CH_3$ | $OCH_3$ | N | |
| $CH(CH_3)CH(CH_3)$ | H | H | $NHCH_3$ | $OCH_3$ | $OCH_3$ | N | |
| $CH(C_2H_5)CH_2$ | H | H | $N_3$ | $CH_3$ | $OCH_3$ | CH | |
| $CH(OCH_3)CH_2$ | H | H | SH | $OCH_3$ | $OCH_3$ | CH | |
| $CH(OCH_3)CH(CH_3)$ | H | H | $SO_2N(CH_2CH_3)_2$ | Cl | $OCH_3$ | CH | |
| $CH(SCH_3)CH_2$ | H | H | SCN | $CH_3$ | $OCH_3$ | N | |
| $CH(SCH_3)CH(CH_3)$ | H | H | $NH(CH_2CH_3)$ | $OCH_3$ | $OCH_3$ | N | |
| $CH(Cl)CH_2$ | H | H | $SO_2N(CH_3)_2$ | $CH_3$ | $OCH_3$ | CH | |
| $CH_2CH_2CH_2$ | H | H | SCN | $OCH_3$ | $OCH_3$ | CH | |
| $CH_2CH_2CH(CH_3)$ | H | H | $N_3$ | $CH_3$ | $OCH_3$ | N | |
| $CH(CH_3)CH_2CH_2$ | H | H | $N(CH_3)_2$ | $OCH_3$ | $OCH_3$ | N | |
| $CH(OCH_3)CH_2CH_2$ | H | H | $SO_2NHCH_3$ | $OCH_3$ | $C_2H_5$ | CH | |
| $CH_2CH_2$ | $CH_3$ | H | SCN | $CH_3$ | $OC_2H_5$ | CH | |
| $CH_2CH_2$ | H | H | $N_3$ | $CH_3$ | $OCH_2Cl$ | CH | |
| $CH_2CH_2$ | H | H | SH | $CH_3$ | $OCH_2CH_2Cl$ | CH | |
| $CH_2CH_2$ | H | H | $SO_2N(CH_3)_2$ | $OCH_3$ | $OCH_2Cl$ | CH | |
| $CH_2CH_2$ | H | H | SCN | $OCH_3$ | $CH_2CH_2Cl$ | CH | |
| $CH_2CH_2$ | H | H | $N_3$ | $CH_3$ | $SCH_2Cl$ | CH | |
| $CH_2CH_2$ | H | H | SH | $OCH_3$ | Br | CH | |
| $CH_2CH_2$ | H | H | $N(CH_3)_2$ | $OCH_3$ | F | CH | |
| $CH_2CH_2$ | H | H | $SO_2NHCH_3$ | $OCH_3$ | I | CH | |
| $CH_2CH_3$ | H | H | SCN | $CH_3$ | $CH_2OCH_3$ | CH | |
| $CH_2CH_3$ | H | H | $N_3$ | $CH_3$ | $CH(OCH_3)_2$ | CH | |
| $CH_2CH_2$ | H | H | SH | 1,3-dioxolan-2-yl | | CH | |
| $CH_2CH_2$ | H | H | $NH(CH_2CH_3)$ | 1,3-dioxan-2-yl | | CH | |
| $CH_2CH_2$ | H | H | SCN | $CH_3$ | $OCH_2OCH_3$ | CH | |
| $CH_2CH_2$ | H | H | $N_3$ | Cl | $NH_2$ | N | |
| $CH_2CH_2$ | H | H | $SO_2NH(CH_2CH_3)$ | $OC_2H_5$ | $NHCH_3$ | N | |
| $CH_2CH_2$ | H | H | $N(CH_3)_2$ | Cl | $N(CH_3)_2$ | N | |

TABLE 4b

General Structure 4b

| Q | R | $R_1$ | $R_2$ | X | Y | Z | m.p. (°C.) |
|---|---|---|---|---|---|---|---|
| $CH_2CH_2$ | H | H | $SO_2N(CH_3)_2$ | $CH_3$ | $CH_3$ | CH | |
| $CH_2CH_2$ | H | H | SCN | $OCH_3$ | $CH_3$ | CH | |
| $CH_2CH_2$ | H | H | $N(CH_3)_2$ | $OCH_3$ | $OCH_3$ | CH | |
| $CH_2CH_2$ | H | H | $N_3$ | Cl | $OCH_3$ | CH | |
| $CH_2CH_2$ | H | H | SH | $CH_3$ | $CH_3$ | N | |
| $CH(CH_3)CH_2$ | H | H | $SO_2NHCH_3$ | $CH_3$ | $OCH_3$ | N | |
| $CH(CH_3)CH(CH_3)$ | H | H | $NHCH_3$ | $OCH_3$ | $OCH_3$ | N | |
| $CH(C_2H_5)CH_2$ | H | H | $N_3$ | $CH_3$ | $OCH_3$ | CH | |
| $CH(OCH_3)CH_2$ | H | H | SH | $OCH_3$ | $OCH_3$ | CH | |
| $CH(OCH_3)CH(CH_3)$ | H | H | $SO_2N(CH_2CH_3)_2$ | Cl | $OCH_3$ | CH | |
| $CH(SCH_3)CH_2$ | H | H | SCN | $CH_3$ | $OCH_3$ | N | |
| $CH(SCH_3)CH(CH_3)$ | H | H | $NH(CH_2CH_3)$ | $OCH_3$ | $OCH_3$ | N | |
| $CH(Cl)CH_2$ | H | H | $SO_2N(CH_3)_2$ | $CH_3$ | $OCH_3$ | CH | |
| $CH_2CH_2CH_2$ | H | H | SCN | $OCH_3$ | $OCH_3$ | CH | |
| $CH_2CH_2CH(CH_3)$ | H | H | $N_3$ | $CH_3$ | $OCH_3$ | N | |

TABLE 4b-continued

General Structure 4b

| Q | R | $R_1$ | $R_2$ | X | Y | Z | m.p. (°C.) |
|---|---|---|---|---|---|---|---|
| $CH(CH_3)CH_2CH_2$ | H | H | $N(CH_3)_2$ | $OCH_3$ | $OCH_3$ | N | |
| $CH(OCH_3)CH_2CH_2$ | H | H | $SO_2NHCH_3$ | $OCH_3$ | $C_2H_5$ | CH | |
| $CH_2CH_2$ | $CH_3$ | H | SCN | $CH_3$ | $OC_2H_5$ | CH | |
| $CH_2CH_2$ | H | H | $N_3$ | $CH_3$ | $OCH_2Cl$ | CH | |
| $CH_2CH_2$ | H | H | SH | $CH_3$ | $OCH_2CH_2Cl$ | CH | |
| $CH_2CH_2$ | H | H | $SO_2N(CH_3)_2$ | $OCH_3$ | $OCH_2Cl$ | CH | |
| $CH_2CH_2$ | H | H | SCN | $OCH_3$ | $CH_2CH_2Cl$ | CH | |
| $CH_2CH_2$ | H | H | $N_3$ | $CH_3$ | $SCH_2Cl$ | CH | |
| $CH_2CH_2$ | H | H | SH | $OCH_3$ | Br | CH | |
| $CH_2CH_2$ | H | H | $N(CH_3)_2$ | $OCH_3$ | F | CH | |
| $CH_2CH_2$ | H | H | $SO_2NHCH_3$ | $OCH_3$ | I | CH | |
| $CH_2CH_3$ | H | H | SCN | $CH_3$ | $CH_2OCH_3$ | CH | |
| $CH_2CH_3$ | H | H | $N_3$ | $CH_3$ | $CH(OCH_3)_2$ | CH | |
| $CH_2CH_2$ | H | H | SH | 1,3-dioxolan-2-yl | | CH | |
| $CH_2CH_2$ | H | H | $NH(CH_2CH_3)$ | 1,3-dioxan-2-yl | | CH | |
| $CH_2CH_2$ | H | H | SCN | $CH_3$ | $OCH_2OCH_3$ | CH | |
| $CH_2CH_2$ | H | H | $N_3$ | Cl | $NH_2$ | CH | |
| $CH_2CH_2$ | H | H | $SO_2NH(CH_2CH_3)$ | $OC_2H_5$ | $NHCH_3$ | N | |
| $CH_2CH_2$ | H | H | $N(CH_3)_2$ | Cl | $N(CH_3)_2$ | CH | |

TABLE 5

General Structure 5

| J | Q | a* | $R_2$ | $R_1$ | R | A | $X_1$ | $X_2$ | $X_3$ | $Y_1$ | $Y_2$ | $Y_3$ |
|---|---|---|---|---|---|---|---|---|---|---|---|---|
| J-1 | $CH_2CH_2$ | — | $SO_2N(CH_3)_2$ | H | H | A-2 | $CH_3$ | — | — | O | — | — |
| J-1 | $CH_2CH_2$ | — | $N(CH_3)_2$ | H | H | A-2 | $OCH_3$ | — | — | O | — | — |
| J-1 | $CH_2CH_2$ | — | SCN | H | $CH_3$ | A-2 | $OC_2H_5$ | — | — | O | — | — |
| J-1 | $CH_2CH_2$ | — | $N_3$ | H | $CH_3$ | A-2 | $OCF_2H$ | — | — | O | — | — |
| J-1 | $CH_2CH_2$ | — | SH | $3-CH_3$ | H | A-3 | $CH_3$ | — | — | — | — | — |
| J-1 | $CH_2CH_2$ | — | $SO_2N(CH_3)_2$ | H | H | A-3 | $OCH_3$ | — | — | — | — | — |
| J-1 | $CH(CH_3)CH_2$ | — | SCN | H | H | A-3 | $OC_2H_5$ | — | — | — | — | — |
| J-1 | $CH_2CH_2CH_2$ | — | $N_3$ | H | H | A-4 | $CH_3$ | — | — | — | $CH_3$ | — |
| J-1 | $CH_2CH_2$ | — | $SO_2N(CH_3)_2$ | $3-OCH_3$ | H | A-4 | $OCH_3$ | — | — | — | H | — |
| J-1 | $CH_2CH(CH_3)$ | — | SH | H | H | A-4 | $OC_2H_5$ | — | — | — | H | — |
| J-1 | $CH_2CH_2$ | — | $NHCH_3$ | H | H | A-5 | — | $OCH_3$ | — | — | — | $CH_3$ |
| J-1 | $CH_2CH_2$ | — | $SO_2NHCH_3$ | H | H | A-5 | — | $CH_3$ | — | — | — | $CH_3$ |
| J-1 | $CH_2CH_2CH_2$ | — | $N_3$ | H | H | A-5 | — | $SCH_3$ | — | — | — | $CH_3$ |
| J-1 | $CH_2CH_2$ | — | $SO_2N(CH_3)_2$ | H | H | A-6 | — | — | $OCH_3$ | — | — | — |
| J-1 | $CH_2CH_2$ | — | $N(CH_3)_2$ | H | H | A-6 | — | — | $CH_3$ | — | — | — |
| J-2 | $3-CH_2CH_2$ | 4 | $N_3$ | H | H | A-4 | $CH_3$ | — | — | — | H | — |
| J-2 | $3-CH_2CH_2$ | 4 | $SO_2N(CH_3)_2$ | H | H | A-2 | $CH_3$ | — | — | O | — | — |
| J-3 | $CH_2CH_2$ | — | SCN | H | H | A-5 | $OCH_3$ | — | — | — | — | $CH_3$ |
| J-4 | $CH_2CH_2$ | — | $NHCH_3$ | H | H | A-6 | — | — | $OCH_3$ | — | — | — | a* = Ring Position of Bridge

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, New York, 1963, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knüsli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Edn., Blackwell Scientific Publications, Oxford, 1968, pp. 101–103.

In the following examples, all parts are by weight unless otherwise indicated.

EXAMPLE 11

Wettable Powder

| | |
|---|---|
| 2-[[(4,6-dimethoxypyrimidin-2-yl)aminocarbonyl]-aminosulfonyl]-N,N—dimethylbenzeneethanesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill to produce an average particle size under 15 microns, reblended, and sifted through a U.S.S. No. 50 sieve (0.3 mm opening) before packaging.

All compounds of the invention may be formulated in the same manner.

EXAMPLE 12

High Strength Concentrate

| | |
|---|---|
| 2-[[(4-methoxy-6-methyl-1,3,5-triazin-2-yl)-aminocarbonyl]aminosulfonyl]-N,N—dimethylbenzeneethanesulfonamide | 98.5% |
| silica aerogel | 0.5% |
| synthetic amorphous silica | 1.5% |

The ingredients are blended and ground in a hammer-mill to produce a high strength concentrate essentially all passing a U.S.S. No. 50 sieve (0.3 mm opening). This material may then be formulated in a variety of ways.

EXAMPLE 13

Granule

| | |
|---|---|
| Wettable Powder of Example 11 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm, (U.S.S. #18 to 40 sieves), the granules are removed, dried, and screened. Oversize material is crushed to produce additional material in the desired range. These granules contain 6% active ingredient.

EXAMPLE 14

Extruded Pellet

| | |
|---|---|
| 2-[[(4,6-dimethoxypyrimidin-2-yl)aminocarbonyl]-aminosulfonyl]-N,N—dimethylbenzeneethanesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dired pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 15

Wettable Powder

| | |
|---|---|
| 2-[[(4-methoxy-6-methyl-1,3,5-triazin-2-yl)amino-carbonyl]aminosulfonyl]-N,N—dimethylbenzeneethanesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer-mill to produce particles essentially all below 100 microns, the material is reblended and sifted through a U.S.S. No. 50 sieve (0.3 mm opening) and packaged.

EXAMPLE 16

Wettable Powder

| | |
|---|---|
| 2-[[(4,6-dimethoxypyrimidin-2-yl)aminocarbonyl]-aminosulfonyl]-N,N—dimethylbenzeneethanesulfonamide | 50% |
| sodium alkylnaphthalenesulfonate | 2% |
| low viscosity methyl cellulose | 2% |

| | |
|---|---|
| -continued | |
| diatomaceous earth | 46% |

The ingredients are blended, coarsely hammer-milled and then air milled to produce particles of active essentially all below 10 microns in diameter. The product is reblended before packaging.

EXAMPLE 17

Oil Suspension

| | |
|---|---|
| 2-[[(4-methoxy-6-methyl-1,3,5-triazin-2-yl)amino-carbonyl]aminosulfonyl]-N,N—dimethylbenzeneethane-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 18

Oil Suspension

| | |
|---|---|
| 2-[[(4,6-dimethoxypyrimidin-2-yl)aminocarbonyl]-aminosulfonyl]-N,N—dimethylbenzeneethane-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 19

Aqueous Suspension

| | |
|---|---|
| 2-[[(4,6-dimethoxypyrimidin-2-yl)aminocarbonyl]-aminosulfonyl]-N,N—dimethylbenzeneethane-sulfonamide | 25% |
| hydrated attapulgite | 3% |
| crude calcium ligninsulfonate | 10% |
| sodium hydrogen phosphate | 0.5% |
| water | 61.5% |

The ingredients are ground together in a ball or roller mill until the solid particles have been reduced to a diameter under 10 microns.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, barley, and cotton. Alternatively, the subject compounds are useful to modify plant growth.

The rates of application for the compounds of the invention are determined by a number of factors, including their use as plant growth regulants or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds $$\text{Ar}-CH_2CH_2R_2, \quad SO_2NHC(O)NH-\text{Het}(X,Y,Z)$$

(benzene ring with CH$_2$CH$_2$R$_2$ and SO$_2$NHC(O)NH– substituents; heterocycle with X, Y, Z and N positions)

| Compound | R$_2$ | X | Y | Z |
|---|---|---|---|---|
| 1 | SO$_2$N(CH$_3$)$_2$ | OCH$_3$ | OCH$_3$ | CH |
| 2 | SO$_2$N(CH$_3$)$_2$ | CH$_3$ | OCH$_3$ | CH |
| 3 | SO$_2$N(CH$_3$)$_2$ | OCH$_3$ | CH$_3$ | N |
| 4 | SCN | OCH$_3$ | Cl | CH |
| 5 | SCN | CH$_3$ | CH$_3$ | N |
| 6 | SCN | OCH$_3$ | OCH$_3$ | CH |
| 7 | SCN | CH$_3$ | CH$_3$ | CH |
| 8 | SCN | CH$_3$ | OCH$_3$ | CH |
| 9 | SCN | CH$_3$ | OCH$_3$ | N |
| 10 | SCN | OCH$_3$ | OCH$_3$ | N |

Test A

Seeds of crabgrass (Digitaria spp.). barnyardgrass (Echinochloa crusgalli), wild oats (Avena fatua), cheatgrass (Bromus secalinus), velvetleaf (Abutilon theophrasti), morningglory (Ipomoea spp.), cocklebur (Xanthium pensylvanicum), sicklepod (Cassia obtusifolia), sorghum, corn, soybean, sugarbeet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;

E=emergence inhibition;
G=growth retardation;
H=formative effect;
U=ususual pigmentation;
X=axillary stimulation;
S=albinism; and
6Y=abscised buds or flowers.

mately fourteen days, then sprayed postemergence with the chemicals dissolved in a non-phytotoxic solvent.

Preemergence

Two rounds pans (25 cm diameter by 12.5 cm deep) were filled with Sassafras sandy loam soil. One pan was planted with blackgrass, sugar beets, nutsedge, crabgrass, sicklepod, teaweed, jimsonweed, velvetleaf, giant

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 |
|---|---|---|---|---|---|---|---|---|---|---|
| POSTEMERGENCE | | | | | | | | | | |
| Morningglory | 9C | 10C | 4C,9G | 3C,8G | 0 | 5C,9G | 0 | 4C,9G | 3C,7G | 4C,7G |
| Cocklebur | 10C | 10C | 5C,9G | 2C,8H | 0 | 9C | 1C | 4C,9H | 4C,8H | 4C,8G |
| Velvetleaf | — | — | — | 3G | 0 | 9C | 4C,8G | 9C | 9C | 4C,9G |
| Nutsedge | 9G | 2C,7G | 0 | 0 | 0 | 4C,9G | 1C | 3C,8G | 0 | 0 |
| Crabgrass | 2C,6G | 4G | 2G | 0 | 0 | 0 | 0 | 3G | 0 | 0 |
| Barnyardgrass | 9C | 4C,9H | 3C,7H | 4G | 0 | 4C,9H | 2C | 3C,8H | 0 | 0 |
| Cheatgrass | — | — | — | 0 | 0 | 5G | 3G | 6G | 0 | 0 |
| Wild Oats | 2C | 2G | 0 | 0 | 0 | 0 | 0 | 2C | 0 | 0 |
| Wheat | 2G | 3G | 0 | 0 | 0 | 0 | 0 | 0 | 0 | 0 |
| Corn | 3C,9H | 3C,9H | 3C,5H | 0 | 0 | 3C,7H | 1C,6G | 3C,7H | 5G | 2H |
| Soybean | 4C,9G | 2C,9G | 3C,8G | 0 | 0 | 3C,9G | 2C,3H | 3C,8H | 4C,9G | 4C,9G |
| Rice | 6G | 7G | 2G | 5G | 0 | 7G | 5G | 6G | 3G | 0 |
| Sorghum | 2C,9G | 3C,9G | 2C,7G | 2C,8H | 0 | 4C,9H | 2C,6G | 4C,9H | 3G | 0 |
| Sugar beet | 9C | 5C,9G | 5C,9G | 3C,8G | 2H | 9C | 3C,8H | 10C | 9C | 10C |
| Cotton | 9C | 5C,9G | 4C,8G | 3C,7G | 0 | 9C | 2C,9G | 9C | 10C | 9C |
| Sicklepod | 9C | 4C,8G | 4C,8H | — | — | — | — | — | — | — |
| PREEMERGENCE | | | | | | | | | | |
| Morningglory | 9C | 9C | 3C,7H | 7G | 0 | 6G | 0 | 4C,5G | 3C,5G | 2C,5G |
| Cocklebur | 9H | 9H | 3C,4H | 0 | 0 | 7G | 0 | 3G | — | 5G |
| Velvetleaf | — | — | — | 7G | 0 | 8G | 0 | 7H | 6G | 2G |
| Nutsedge | 4C,9G | 10E | 0 | 0 | 0 | 2C,5G | 0 | 2C,5G | 0 | 0 |
| Crabgrass | 2C | 0 | 0 | 0 | 0 | 1C | 0 | 1H | 0 | 0 |
| Barnyardgrass | 3C,9H | 3C,8H | 0 | 0 | 0 | 2C,6H | 0 | 3C,7H | 0 | 0 |
| Cheatgrass | — | — | — | 0 | 0 | 2C,9G | 0 | 7G | 0 | 0 |
| Wild Oats | 2C,8G | 2C,8G | 0 | 0 | 0 | 2C | 0 | 7G | 0 | 0 |
| Wheat | 4G | 6G | 0 | 0 | 0 | 2G | 0 | 5G | 0 | 0 |
| Corn | 2C,9G | 5C,9H | 2C,5G | 5G | 0 | 2C,6G | 3G | 3C,8H | 5G | 0 |
| Soybean | 6H | 2C,8H | 1C | 0 | 0 | 2C,5H | 0 | 3C,4H | 1C,1H | 1H |
| Rice | 7G | 3C,8H | 2G | 4G | 0 | 3C,8G | 5G | 4C,7G | 0 | 0 |
| Sorghum | 10H | 10H | 2C,7G | 4G | 0 | 3C,9H | 3C,7H | 5C,9H | 0 | 0 |
| Sugar beet | 5C,9G | 10E | 3C,8G | 8G | 6G | 4C,9G | 4G | 5C,9G | 4C,9G | 8G |
| Cotton | 7G | 9G | 2C,5G | 5G | 0 | 8G | 0 | 8G | 8G | 5G |
| Sicklepod | 4C,9G | 3C,9G | 3C | — | — | — | — | — | — | — |

Test B

Postemergence

Two round pans (25 cm diameter by 12.5 cm deep) were filled with Sassafras sandy loam soil. One pan was planted with blackgrass, (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), giant foxtail (*Setaria faberii*) and rape (*Brassica napus*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately foxtail and rape. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

In some tests response ratings are based on a scale of 0 to 10: where 0=no effect, and 10=complete control. The type of response is indicated by letters where G=growth retardation and C=chlorosis/necrosis.

In other tests the response is rated on a scale of 0-100 with 0=no injury and 100=complete control. In these tests the type of response is not indicated.

Response ratings are contained in Table B.

TABLE B

| | Compound 1 | | | Compound 2 | | | | Compound 3 | | Compound 6 | | | Compound 8 | | |
|---|---|---|---|---|---|---|---|---|---|---|---|---|---|---|---|---|
| Rate g/ha | 62 | 16 | 4 | 62 | 16 | 4 | 1 | 62 | 16 | 62 | 16 | 4 | 250 | 62 | 16 |
| POSTEMERGENCE | | | | | | | | | | | | | | | | |
| Corn | 8G | 3G | 0 | 3G | 0 | 0 | 90 | 60 | 20 | 0 | 0 | 100 | 20 | 0 | 100 | 60 | 0 |
| Wheat | 0 | 0 | 0 | 0 | 0 | 0 | 0 | 0 | 0 | 0 | 0 | 0 | 0 | 0 | 0 | 0 | 0 |
| Rice | 4G | 0 | 0 | 3G | 0 | 0 | 70 | 30 | 0 | 0 | 0 | 20 | 0 | 0 | 30 | 0 | 0 |
| Soybean | 9G | 8G | 5G | 7G | 4G | 2G | 80 | 60 | 20 | 0 | 4G | 2G | 100 | 40 | 50 | 100 | 70 | 20 |
| Cotton | 7G | 6G | 0 | 6G | 2G | 0 | 90 | 70 | 40 | 0 | 7G | 3G | 80 | 40 | 20 | 80 | 40 | 0 |
| Sugar beet | 9G | 9G | 6G | 10G | 8G | 5G | 100 | 100 | 100 | 50 | 6G | 3G | 90 | 90 | 80 | 100 | 60 | 50 |
| Rape | — | — | — | — | — | — | 100 | 100 | 100 | 70 | — | — | 100 | 90 | 90 | 100 | 100 | 90 |

TABLE B-continued

|  | Compound 1 | | | Compound 2 | | | Compound 3 | | | Compound 6 | | Compound 8 | | |
|---|---|---|---|---|---|---|---|---|---|---|---|---|---|---|
| Crabgrass | 6G | 3G | 0 | 3G | 0 | 0 | 0 | 0 | 0 | 0 | 3G | 0 | 0 | 0 | 0 | 20 | 0 | 0 |
| Johnsongrass | 9G | 8G | 4G | 8G | 6G | 2G | 90 | 30 | 0 | 0 | 6G | 2G | 0 | 0 | 0 | 90 | 60 | 20 |
| Blackgrass | 8G | 6G | 0 | 6G | 4G | 0 | 70 | 20 | 0 | 0 | 2G | 0 | 80 | 0 | 0 | 80 | 20 | 0 |
| Barnyardgrass | 9G | 7G | 4G | 6G | 3G | 0 | 90 | 40 | 0 | 0 | 4G | 0 | 100 | 30 | 0 | 90 | 60 | 0 |
| Nutsedge | 7G | 3G | 0 | 6G | 2G | 0 | 0 | 0 | 0 | 0 | 0 | 0 | 100 | 90 | 80 | 40 | 0 | 0 |
| Giant Foxtail | 7G | 3G | 0 | 6G | 0 | 0 | 30 | 0 | 0 | 0 | 5G | 0 | 0 | 0 | 0 | 0 | 0 | 0 |
| Wild Oats | 3G | 0 | 0 | 0 | 0 | 0 | 0 | 0 | 0 | 0 | 0 | 0 | 0 | 0 | 0 | 70 | 0 | 0 |
| Cocklebur | 10G | 8G | 4G | 9G | 7G | 3G | 80 | 60 | 30 | 0 | 9G | 7G | 100 | 80 | 40 | 90 | 70 | 40 |
| Morningglory | 7G | 3G | 0 | 7G | 4G | 0 | 100 | 100 | 50 | 0 | 7G | 4G | 90 | 90 | 60 | 100 | 90 | 80 |
| Teaweed | 4G | 0 | 0 | 3G | 0 | 0 | 30 | 0 | 0 | 0 | 3G | 0 | 20 | 0 | 0 | 50 | 0 | 0 |
| Sicklepod | 9G | 4G | 0 | 8G | 3G | 0 | 60 | 50 | 0 | 0 | 0 | 0 | 100 | 80 | 60 | 90 | 80 | 50 |
| Jimsonweed | 9G | 9G | 4G | 9G | 3G | 0 | 80 | 50 | 20 | 0 | 4G | 0 | 0 | 0 | 0 | 80 | 30 | 0 |
| Velvetleaf | 9G | 7G | 2G | 8G | 3G | 0 | 100 | 100 | 30 | 0 | 0 | 0 | 100 | 70 | 20 | 100 | 90 | 60 |

|  | Compound 1 | | | Compound 2 | | | Compound 3 | | | Compound 6 | | | Compound 8 | |
|---|---|---|---|---|---|---|---|---|---|---|---|---|---|---|
| Rate g/ha | 250 | 62 | 16 | 250 | 62 | 16 | 250 | 62 | 16 | 250 | 62 | 16 | 250 | 62 |
| | | | | | PREEMERGENCE | | | | | | | | | |
| Corn | 9G | 5G | 0 | 8G | 2G | 0 | 100 | 50 | 0 | 4G | 2G | 70 | 20 | 0 | 60 | 0 |
| Wheat | 0 | 0 | 0 | 0 | 0 | 0 | 0 | 0 | 0 | 0 | 0 | 0 | 0 | 0 | 0 | 0 |
| Rice | 9G | 5G | 0 | 8G | 5G | 0 | 100 | 90 | 50 | 5G | 0 | 100 | 60 | 0 | 90 | 40 |
| Soybean | 7G | 2G | 0 | 6G | 3G | 0 | 70 | 30 | 0 | 0 | 0 | 70 | 20 | 0 | 30 | 0 |
| Cotton | 4G | 0 | 0 | 5G | 2G | 0 | 20 | 0 | 0 | 8G | 2G | 40 | 0 | 0 | 0 | 0 |
| Sugar beet | 10G | 9G | 6G | 10G | 5G | 3G | 100 | 100 | 60 | 7G | 4G | 100 | 50 | 0 | 90 | 60 |
| Rape | — | — | — | — | — | — | 100 | 100 | 30 | — | — | 100 | 90 | 50 | 90 | 50 |
| Crabgrass | 7G | 4G | 0 | 4G | 0 | 0 | 50 | 0 | 0 | 0 | 0 | 40 | 0 | 0 | 0 | 0 |
| Johnsongrass | 10G | 9G | 8G | 9G | 6G | 2G | 90 | 60 | 30 | 6G | 3G | 90 | 30 | 0 | 90 | 30 |
| Blackgrass | 10G | 9G | 8G | 9G | 8G | 4G | 90 | 60 | 0 | 8G | 7G | 80 | 40 | 0 | 50 | 0 |
| Barnyardgrass | 9G | 8G | 5G | 8G | 5G | 2G | 80 | 60 | 0 | 4G | 0 | 80 | 20 | 0 | 60 | 0 |
| Nutsedge | 8G | 7G | 0 | 0 | 0 | 0 | 100 | 40 | 0 | 0 | 0 | 50 | 0 | 0 | 0 | 0 |
| Giant Foxtail | 9G | 9G | 3G | 8G | 4G | 2G | 90 | 40 | 0 | 4G | 0 | 20 | 0 | 0 | 0 | 0 |
| Wild Oats | 5G | 3G | 0 | 0 | 0 | 0 | 0 | 0 | 0 | 0 | 0 | 0 | 0 | 0 | 0 | 0 |
| Cocklebur | 8G | 6G | 3G | 9G | 8G | 2G | 80 | 30 | 0 | 8G | 2G | 0 | 0 | 0 | 20 | 0 |
| Morningglory | 7G | 3G | 2G | 6G | 3G | 0 | 60 | 30 | 0 | 8G | 3G | 0 | 0 | 0 | 20 | 0 |
| Teaweed | 9G | 5G | 0 | 8G | 5G | 2G | 100 | 90 | 30 | 0 | 0 | 90 | 30 | 0 | 0 | 0 |
| Sicklepod | 5G | 0 | 0 | 4G | 0 | 0 | 60 | 20 | 0 | 0 | 0 | 40 | 0 | 0 | 0 | 0 |
| Jimsonweed | 9G | 5G | 2G | 7G | 3G | 0 | 100 | 30 | 0 | 5G | 2G | 80 | 0 | 0 | 0 | 0 |
| Velvetleaf | 8G | 3G | 0 | 5G | 3G | 0 | 60 | 30 | 0 | 6G | 0 | 80 | 30 | 0 | 50 | 0 |

Test C

Two ten-inch in diameter plastic pans lined with polyethylene liners were filled with prepared silt loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), rapeseed (*Brassica napus*) and Italian ryegrass (*Lolium multiflorum*). The other pan was planted with seeds of Russian thistle (*Salsola kali*), kochia (*Kochia scoparia*), speedwell (*Veronica persica*), shepherd's purse (*Capsella bursa-pastoris*), *Matricaria inodora*, black nightshade (*Solanum nigrum*) and wild buckwheat (*Polygonum convolvulus*). The above two pans were treated preemergence. At the same time two pans in which the above plant species were growing were treated postemergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C. Ratings are based on a scale of 0 to 10 where 0=no effect and 10=complete control. The type of response is indicated by letters where G=growth retardation and C=chlorosis/necrosis.

TABLE C

|  | Compound 1 | | | | | |
|---|---|---|---|---|---|---|
| Rate g/ha | 125 | 64 | 32 | 16 | 8 | 4 | 2 |
| | POSTEMERGENCE | | | | | | |
| wheat | 7G | 5G | 3G | 2G | 1G | 0 | 0 |
| barley | 8G | 7G | 6G | 4G | 3G | 0 | 0 |
| sugar beets | 9G | 8G | 9G | 7G | 4G | 4G | 4G |
| rapeseed | 10C | 9G | 10C | 6G | 6G | 6G | 4G |
| wild oats | 10C | 10C | 7G | 4G | 0 | 0 | 0 |
| cheatgrass | 10C | 10C | 2G | 0 | 0 | 0 | 0 |
| blackgrass | 8G | 7G | 3G | 0 | 0 | 0 | 0 |
| annual bluegrass | 6G | 4G | 0 | 0 | 0 | 0 | 0 |
| green foxtail | 5G | 3G | 0 | 0 | 0 | 0 | 0 |
| Italian ryegrass | 10C | 10C | 4G | 2G | 0 | 0 | 0 |
| Matricaria inodora | 10C | 10C | 10C | 10C | 9G | 5G | 5G |
| galium | 9G | 9G | 8G | 5G | 8G | 0 | 0 |
| Russian thistle | 10C | 10C | 6G | 3G | 6G | 0 | 0 |
| shepherd's purse | 10C | 10C | 10C | 10C | 10C | 5G | 5G |
| kochia | 10C | 9G | 7G | 4G | 8G | 0 | 0 |
| black nightshade | 4G | 3G | 0 | 0 | 0 | 0 | 0 |
| speedwell | 3G | 3G | 0 | 0 | 0 | 0 | 0 |
| wild buckwheat | 6G | 5G | 0 | 0 | 0 | 0 | 0 |
| | PREEMERGENCE | | | | | | |
| wheat | 7G | 4G | 2G | 0 | 0 | 0 | 0 |
| barley | 10C | 9G | 9G | 7G | 3G | 2G | 0 |
| sugar beets | 10C | 10C | 9G | 8G | 7G | 6G | 5G |
| rapeseed | 10C | 9G | 9G | 4G | 0 | 0 | 0 |
| wild oats | 10C | 6G | 0 | 0 | 0 | 0 | 0 |
| cheatgrass | 8G | 8G | 4G | 2G | 0 | 0 | 0 |
| blackgrass | 10C | 8G | 4G | 4G | 6G | 3G | 0 |
| annual bluegrass | 8G | 6G | 0 | 0 | 0 | 0 | 0 |
| green foxtail | 7G | 3G | 0 | 0 | 0 | 0 | 0 |
| Italian ryegrass | 10C | 9G | 0 | 0 | 0 | 0 | 0 |
| Matricaria inodora | 9G | 9G | 8G | 5G | 3G | 5G | 2G |
| galium | 9G | 9G | 8G | 7G | 0 | 0 | 0 |
| Russian thistle | 10C | 8G | 4G | 0 | 0 | 0 | 0 |
| shepherd's purse | 8G | 7G | 7G | 5G | 7G | 5G | 5G |
| kochia | 10C | 10C | 6G | 4G | 0 | 0 | 0 |
| black nightshade | 4G | 2G | 0 | 0 | 0 | 0 | 0 |
| speedwell | 7G | 4G | 2G | 0 | 0 | 0 | 0 |

TABLE C-continued

| Rate g/ha | Compound 1 | | | | | | |
|---|---|---|---|---|---|---|---|
| | 125 | 64 | 32 | 16 | 8 | 4 | 2 |
| wild buckwheat | 7G | 3G | 3G | 0 | 0 | 0 | 0 |

Test D

Sixteen-cm diameter Wagner pots, equipped with a stoppered drain opening near the bottom of the side wall, were partially filled with Sassafras sandy loam. About 1500 ml of water were added to each pot to bring the water level to a point 3 cm above the soil surface. Japonica and Indica rice seedlings were transplanted as described in Test C. Also, a number of barnyardgrass (*Echinochloa crusgalli*) seeds were added to each pot. At the same time, seedlings or tubers of the following species were transplanted into the muddy soil: water plantain (*Alisma trivale*), Scirpus (*Scirpus mucranatus*), monochoria vaginalis and Cyperus (*Cyperus difformis*). The weed species selected for this test are of ecomomic importance in major rice-growing areas. The chemical treatments were applied as described in Test C, within hours after transplanting of two additional species: water chestnut (*Eleocharis spp.*) and arrowhead (*Sagittaria latifolia*). Shortly after treatment, the drain hole was opened to drop the water level by two cm. Water was then added to restore the water level to its original height. The following day the draining and refilling process was repeated. The pots were then maintained in the greenhouse. Rates of application and plant response ratings made 21 days after treatment are summarized in Table D. Response ratings are based on a scale of 0–100 where 0=no injury and 100=complete control.

TABLE D

| Rate g/ha | Compound 1 | | | | | | |
|---|---|---|---|---|---|---|---|
| | 125 | 63 | 63 | 30 | 30 | 16 | 8 |
| Japonica Rice | 37 | 20 | 20 | 20 | 0 | 0 | 0 |
| Indica Rice | 50 | 20 | 20 | 20 | 0 | 0 | 0 |
| Barnyardgrass | 100 | 95 | 100 | 95 | 95 | 82 | 87 |
| Water Chesnut | 100 | 97 | 100 | 95 | 95 | 92 | 82 |
| Arrowhead | 100 | 100 | 100 | 95 | 97 | 92 | 77 |
| Scirpus | 100 | 97 | 100 | 97 | 100 | 90 | 75 |
| Cyperus | 100 | 95 | 100 | 95 | 100 | 92 | 75 |
| Water Plantain | 100 | 90 | 100 | 50 | 97 | 25 | 0 |
| Monochoria | — | 100 | — | 100 | — | 100 | 100 |

What is claimed is:

1. A compound of formula:

$$JSO_2NHCNA$$
$$\underset{R}{|}\;\; \overset{O}{\underset{\|}{}}$$

I wherein

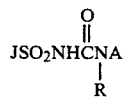

J-2

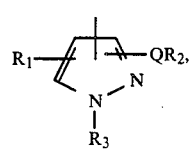

J-3

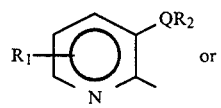

J-4

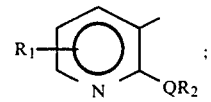

R is H or $CH_3$;

$R_1$ is H, $C_1$-$C_3$ alkyl, $C_1$-$C_3$ haloalkyl, halogen, nitro, $C_1$-$C_3$ alkoxy, $SO_2NR_aR_b$, $C_1$-$C_3$ alkylthio, $C_1$-$C_3$ alkylsulfinyl, $C_1$-$C_3$ alkylsulfonyl, CN, $CO_2R_c$, $C_1$-$C_3$ haloalkoxy or $C_1$-$C_3$ haloalkylthio;

$R_a$ is H, $C_1$-$C_4$ alkyl, $C_2$-$C_3$ cyanoalkyl, methoxy or ethoxy;

$R_b$ is H, $C_1$-$C_4$ alkyl or $C_3$-$C_4$ alkenyl; or $R_a$ and $R_b$ may be taken together as $-(CH_2)_3-$, $-(CH_2)_4-$, $-(CH_2)_5-$ or $-CH_2CH_2OCH_2CH_2-$;

$R_c$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;

Q is $-(CH_2)_n-$ which may be optionally substituted with 1-3 substituents selected from the group consisting of $C_1$-$C_3$ alkyl, $C_1$-$C_3$ alkoxy, $C_1$-$C_3$ haloalkyl, $C_1$-$C_3$ thioalkyl, halogen, cyano or $NO_2$;

n is 1, 2 or 3;

$R_2$ is $SO_2NR_4R_5$, $NR_4R_5$, SCN, SH or $N_3$;

$R_3$ is H, $C_1$-$C_3$ alkyl or phenyl;

$R_4$ and $R_5$ are independently H, $C_1$-$C_4$ alkyl, $C_1$-$C_4$ haloalkyl, $C_3$-$C_6$ cycloalkyl, $C_2$-$C_4$ alkoxyalkyl, $C_2$-$C_4$ alkylthioalkyl, $C_2$-$C_4$ cyanoalkyl, $C_1$-$C_3$ alkoxy, $C_3$-$C_4$ alkenyl or $C_3$-$C_4$ alkynyl; or $R_4$ and $R_5$ may be taken together to form $-(CH_2)_3-$, $-(CH_2)_4-$, $-(CH_2)_5-$ or $-CH_2CH_2OCH_2CH_2-$;

A is

A-1

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_3$-$C_5$ cycloalkyl, $C_2$-$C_4$ alkynyl or $N(OCH_3)CH_3$;

Z is CH;

and their agriculturally suitable salts; provided that
  (a) when X is Cl, F, Br or I, then Y is $OCH_3$, $OC_2H_5$, $N(OCH_3)CH_3$, $NHCH_3$, $N(CH_3)_2$ or $OCF_2H$;
  (b) when $R_2$ is $SO_2NR_4R_5$, $NR_4R_5$ or SH, then n is 2 or 3; and
  (c) when J is $J_2$, then the substituent $QR_2$ and the sulfonylurea bridge are on adjacent carbon atoms.

2. A compound of claim 1 where
  A is A-1;

$R_1$ is H, $C_1$-$C_2$ alkyl, F, Cl, Br, $C_1$-$C_2$ alkoxy, $C_1$-$C_2$ alkylthio or $C_1$-$C_2$ haloalkoxy;

Q is $CH_2CH_2$ or $CH_2CH_2CH_2$;

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$; and Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $OCF_2H$, $SCF_2H$, cyclopropyl, $C\equiv CH$ or $C\equiv CCH_3$.

3. A compound of claim 2 where Q is $CH_2CH_2$; and $R_4$ and $R_5$ are independently H, $C_1$-$C_3$ alkyl, $C_3$-$C_4$ alkenyl or $C_3$-$C_4$ alkynyl.

4. A compound of claim 3 wherein J is J-2.

5. A compound of claim 3 where J is J-3 or J-4.

6. A compound of claim 1 where $R_2$ is SH, SCN or $N_3$.

7. A compound of claim 6 where

A is A-1;

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$;

Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $OCF_2H$, $SCF_2H$, cyclopropyl, $C\equiv CH$ or $C\equiv CCH_3$;

$R_1$ is H, $C_1$-$C_2$ alkyl, F, Cl, Br, $C_1$-$C_2$ alkoxy, $C_1$-$C_2$ alkylthio or $C_1$-$C_2$ haloalkoxy; and Q is $CH_2CH_2$ or $CH_2CH_2CH_2$.

8. A compound of claim 7 where J is J-2.

9. A compound of claim 7 where J is J-3 or J-4.

10. A composition suitable for controlling the growth of undesired vegetation which comprises an effective amount of a compound of claim 1 and at least one of the following: surfactant, solid or liquid diluent.

11. A composition suitable for controlling the growth of undesired vegetation which comprises an effective amount of a compound of claim 7 and at least one of the following: surfactant, solid or liquid diluent.

12. A method for controlling the growth of undesired vegetation which comprises applying to the locus to be protected an effective amount of a compound of claim 1.

13. A method for controlling the growth of undesired vegetation which comprises applying to the locus to be protected an effective amount of a compound of claim 7.

14. A method for controlling the growth of undesired vegetation which comprises applying to the locus to be protected an effective amount of the compound of claim 13.

* * * * *